: US 9,249,426 B2
(45) Date of Patent: Feb. 2, 2016

(54) LENTIVIRAL VECTORS PSEUDOTYPED WITH MUTANT BAEV GLYCOPROTEINS

(71) Applicants: Anais Girard-Gagnepain, Lyons (FR); Els Verhoeyen, Lyons (FR); Dimitri Lavillette, Lyons (FR); Francois-Loic Cosset, Lyons (FR)

(72) Inventors: Anais Girard-Gagnepain, Lyons (FR); Els Verhoeyen, Lyons (FR); Dimitri Lavillette, Lyons (FR); Francois-Loic Cosset, Lyons (FR)

(73) Assignees: Institut National de la Sante et de la Recherche Medicale (INSERM), Paris (FR); Ecole Normale Superieur de Lyon, Lyons (FR)

( * ) Notice: Subject to any disclaimer, the term of this patent is extended or adjusted under 35 U.S.C. 154(b) by 0 days.

(21) Appl. No.: 14/346,357

(22) PCT Filed: Sep. 28, 2012

(86) PCT No.: PCT/EP2012/069230
§ 371 (c)(1),
(2) Date: Mar. 21, 2014

(87) PCT Pub. No.: WO2013/045639
PCT Pub. Date: Apr. 4, 2013

(65) Prior Publication Data
US 2014/0235700 A1  Aug. 21, 2014

(30) Foreign Application Priority Data
Sep. 29, 2011  (EP) .................................... 11306247

(51) Int. Cl.
*A01N 63/00* (2006.01)
*C12N 15/86* (2006.01)
*C07K 14/005* (2006.01)
*A61K 48/00* (2006.01)

(52) U.S. Cl.
CPC .............. *C12N 15/86* (2013.01); *C07K 14/005* (2013.01); *A61K 48/00* (2013.01); *C07K 2319/00* (2013.01); *C12N 2740/13022* (2013.01); *C12N 2740/15043* (2013.01); *C12N 2740/15045* (2013.01); *C12N 2740/16043* (2013.01); *C12N 2740/16045* (2013.01); *C12N 2810/6054* (2013.01)

(58) Field of Classification Search
None
See application file for complete search history.

(56) References Cited

U.S. PATENT DOCUMENTS 7,135,339 B2 * 11/2006 McCray et al. ............... 435/456
7,198,950 B2 *  4/2007 Trono et al. .................. 435/456

FOREIGN PATENT DOCUMENTS

WO    03/091442    11/2003
WO  2009/013324     1/2009

OTHER PUBLICATIONS

Sandrin et al. Blood 2002;100:823-32.*
Tailor et al. J Virol 1999;73:4470-4.*
Aguilar et al. J Virol 2003;77:1281-91.*
Lavillette et al., "The envelope glycoprotein of human endogenous retrovirus type W uses a divergent family of amino acid transporters/cell surface receptors", Journal of Virology, Jul. 1, 2002, pp. 6442-6452, vol. 76, No. 13, The American Society for Microbiology.
Verhoeyen et al., "Novel lentiviral vectors displaying early-acting cytokines selectively promote survival and transduction of NOD/SCID repopulating hematopoietic cells", Blood, Nov. 15, 2005, pp. 3386-3395, vol. 106, No. 10, American Society of Hematology, US.
Frecha et al., "Advances in the field of lentivector-based transduction of T and B lymphocytes for gene therapy", Molecular Therapy, Oct. 1, 2010, pp. 1748-1757, vol. 18, No. 10, Academic Press, San Diego, CA.
Cartier et al., "Hematopoietic Stem Cell Gene Therapy with a Lentiviral Vector in X-Linked Adrenoleukodystrophy", Science, Nov. 6, 2009, pp. 818-823, vol. 326, No. 5954.
Hayakawa et al., "Transient in vivo beta-globin production after lentiviral gene transfer to hematopoietic stem cells in the non-human primate", Human Gene Therapy, Jan. 1, 2009, pp. 563-572, vol. 20, New York, NY, US.
Girard et al., "A Lentiviral Vector Pseudotyped with a Baboon Retrovirus Envelope Glycoprotein Outperforms VSV-G-LVs for Gene Transfer into Hematopoietic Stem Cells and Resting Lymphocytes", Molecular Therapy, May 2012, p. S1, vol. 20, No. suppl 1.

* cited by examiner

*Primary Examiner* — Janice Li
(74) *Attorney, Agent, or Firm* — Whitham Curtis Christofferson & Cook, PC

(57) ABSTRACT

The present invention concerns a pseudotyped viral vector particle for transferring biological material into cells, wherein said vector particle comprises at least:—a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein; or—a modified BaEV envelope glycoprotein wherein the cytoplasmic tail domain is devoid of the fusion inhibitory R peptide.

13 Claims, 14 Drawing Sheets

LENTIVIRAL VECTORS PSEUDOTYPED WITH MUTANT BAEV GLYCOPROTEINS

The present invention concerns pseudotyped lentiviral vectors enabling efficient gene transfer of hematopoietic cells.

Gene therapy holds promise for the cure of many inherited and acquired diseases as evidenced by the success in treatment of X-linked severe combined immunodeficiency (SCID-X1), adenosine desaminase (ADA) deficiency and chronic granulomatous disease. Recently, the successful treatment of patients suffering from X-linked adrenoleukodystrophy (ALD) using lentiviral vectors was reported. In this trial, hematopoietic stem cell (HSC) based gene therapy was able to stop progression of the disease in two patients suffering from this fatal demyelinating disease of the central nervous system. Importantly, for the correction of all these defects of the hematopoietic system, the therapeutic gene must be delivered to cells able both to self-renew and to differentiate into all hematopoietic lineages. Since HSCs answer to these criteria they represent 'the' attractive candidates for gene therapy applications.

However, a major barrier in lentiviral vector transduction of HSC is that 75% of HSC are residing into the $G_0$ phase of the cell cycle and are not very permissive for classical lentiviral vector transduction. This limitation hampers the application of conventional lentiviral vectors for HSC gene therapy, as they do not allow efficient gene transfer into a subpopulation of quiescent ($G_0$) HSCs (Sutton et al. (1999) *J. Virol.* 73:3649-3660). To overcome this limitation, many studies using lentiviral vectors for hCD34$^+$ cell transduction employed a high vector input and the presence of very strong cytokine cocktails (TPO, SCF, Flk-3, IL-6, IL-3) in order to induce HSC cycle entry. Very often, retronectin, a fragment of fibronectin, is used to colocalize vector particles and targeted cells or multiple administrations of vector are applied to achieve high gene transfer rates in HSCs. However, an undesirable effect of extended cytokine stimulation is a decrease of the multi-potentiality and long-term engraftment of human HSCs. Moreover, a too high vector dose poses the risk for multi-copy integration, and in particular for insertional mutagenesis.

There is therefore a need for viral vectors enabling transduction of quiescent HSCs and limiting the risk of multi-copy integration.

Efficient gene transfer into quiescent T and B lymphocytes for gene therapy or immunotherapy purposes may allow the treatment of several genetic dysfunctions of the hematopoietic system, such as immunodeficiencies, and the development of novel therapeutic strategies for cancers and acquired diseases. Lentiviral vectors (LV) are not able to transduce some particular quiescent cell types such as resting T and B cells (Bovia et al. (2003) *Blood* 101:1727-1733; Verhoeyen et al. (2003) *Blood* 101:2167-2174). In T cells, completion of reverse transcription, nuclear import and subsequent integration of the genome of lentiviral vectors pseudotyped with the envelope glycoprotein of the vesicular stomatitis virus (VSV-G) do not occur efficiently unless they are activated via the T-cell receptor or by survival-cytokines inducing them to enter into the $G_{1b}$ phase of the cell cycle. Lentiviral transduction of B cells is another matter since even B-cell receptor (BCR)-stimulation inducing proliferation is not sufficient to allow efficient transduction with VSV-G pseudotyped lentiviral vectors (VSV-G-LVs).

There is therefore an important need for viral vectors enabling transduction of resting T and B cells.

In order to deliver genes by a lentiviral vector in hematopoietic cells, an "entry" envelope protein allowing an efficient vector-cell fusion needs to be presented at its surface. The process of incorporating a heterologous envelope glycoprotein on the core of a lentiviral vector is called "peudotyping". For a long time, VSV-G associated with viral cores derived from HIV-1 has been used. Nevertheless, there are disadvantages in using VSV-G-LVs. Toxicity is associated with long-term expression of VSV-G which makes generation of stable cell lines difficult. In addition, VSV-G-LVs are sensitive to human complement, which makes them unsuited for in vivo use. Only high VSV-G-LVs doses (multiplicity of infection=MOI of 50-100) allow efficient hCD34$^+$ cell transduction increasing the risk of multi-copy integration and thus genotoxicity (Di Nunzio et al. (2007) *Hum. Gene Ther.* 18:811-820). Human beings may also develop strong immune responses against VSV-G which may reduce the efficacy of a second administration of VSV-G-LVs. All these evidences limit ex vivo and in vivo use of VSV-G-LVs.

The chimeric envelope glycoprotein comprising the extracellular and transmembrane domains of the RD114 feline leukemia virus envelope glycoprotein fused to the cytoplasmic tail (designated TR) of the murine leukemia virus A (MLV-A) envelope glycoprotein, called herein after RD114/TR and described in the international application WO 03/091442) appeared to be a quite good alternative envelope. Indeed, this pseudotype is not sensitive to the human complement system which makes it attractive for in vivo applications. RD114/TR-LVs allow efficient transduction of human and macaque CD34$^+$ cells. However, transduction levels stay way below those of VSV-G-LVs and titers of RD114 are much lower than for VSV-G-LVs. Additionally, RD114/TR glycoprotein cannot enter efficiently into murine cells. So this receptor specificity limits the potentialities of work with this LV since the majority of preclinical disease models eligible for gene therapy are mice models.

The present invention arises from the unexpected finding by the inventors that lentiviral vectors pseudotyped with either a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein; or a modified BaEV envelope glycoprotein wherein the cytoplasmic tail domain is devoid of the fusion inhibitory R peptide, display transduction properties particularly suitable for gene transfer into hematopoietic cells, including HSC and resting T and B cells. Indeed, these new LV pseudotypes can transduce very efficiently and stably hCD34$^+$ cells up to 70% at low vector doses and upon mild cytokine stimulation. BaEV-LVs outperformed by far VSV-G and RD114/TR-LVs for the transduction of macaque and human CD34$^+$ cells. Additionally, the inventors showed that BaEV-LVs transduced very early progenitor hCD34$^+$ cells including HSCs since these cells were able to reconstitute an immunodeficient mice model and high level of transduced blood cells were found in several hematopoietic tissues and in those tissues in the different blood cell lineages. Importantly BaEV-LVs were able to transduce IL-7 prestimulated memory and naive T cells at high levels. Moreover, in contrast to VSV-G-LVs and RD114/TR-LVs, these BaEV-LVs also allowed high level transduction of resting and BCR stimulated B cells without induction of a phenotypic switch.

The present invention thus concerns a pseudotyped viral vector particle for transferring biological material into cells, wherein said vector particle comprises at least:
  a chimeric envelope glycoprotein which comprises or consists in a fusion of the transmembrane and extracellular domain of a baboon endogenous retrovirus (BaEV)

envelope glycoprotein and the cytoplasmic tail domain of a murine leukemia virus (MLV) envelope glycoprotein; or a modified BaEV envelope glycoprotein wherein the cytoplasmic tail domain is devoid of the fusion inhibitory R peptide.

The present invention also concerns the pseudotyped viral vector particle according to the invention for use in the treatment of a hematopoietic disorder.

Another object of the invention concerns a medicament comprising a pseudotyped viral vector particle according to the invention as active ingredient.

The invention also relates to the use of a pseudotyped viral vector particle according to the invention for transferring the biological material into hematopoietic cells ex vivo.

Another object of the invention concerns a method for transducing a hematopoietic cell comprising contacting the hematopoietic cell with a pseudotyped viral vector particle according to the invention under conditions to effect the transduction of the hematopoietic cell by the pseudotyped viral vector particle.

The invention also concerns a stable virus packaging cell line producing the pseudotyped viral vector particle as defined above.

DETAILED DESCRIPTION OF THE INVENTION

Pseudotyped Viral Vector Particle

The present invention concerns a pseudotyped viral vector particle for transferring biological material into cells, wherein said vector particle comprises at least:

a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein; or a modified BaEV envelope glycoprotein wherein the cytoplasmic tail domain is devoid of the fusion inhibitory R peptide.

As intended herein, the term "vector particle" denotes any particle liable to display the chimeric envelope glycoprotein or the modified BaEV envelope glycoprotein at its surface and to reversibly bind to a biological material. It is preferred that such a vector particle is a viral vector particle, in particular a retroviral vector particle. Preferably, said retroviral vector particle is selected from the group consisting of an oncoviral vector particle, including murine leukemia virus (MLV), avian leukosis virus (ALV), respiratory syncytial virus (RSV) or Mason-Pfizer monkey virus (MPMV) vector particles, a lentiviral vector particle, such as Human Immunodeficiency Virus (HIV), e.g. HIV-1 or HIV-2, Simian Immunodeficiency Virus (SIV), feline immunodeficiency virus (FIV), equine infectious anemia virus (EIAV) and caprine arthritis encephalitis virus (CAEV) vector particles, and a spumaviral vector particle such as human foamy virus (HFV) vector particle.

Lentiviral vector particles are well-known to the skilled person and are notably described in Naldini et al. (2000) *Adv. Virus. Res.* 55:599-609 and Negre et al. (2002) *Biochimie* 84:1161-1171. Usually, lentiviral vector particles according to the invention comprise at least the following components: (i) an envelope component, which is constituted of a phospholipidic bilayer associated to envelope proteins, wherein the envelope proteins comprise at least the above-defined chimeric or modified glycoproteins, said envelope surrounding (ii) a core component, constituted of the association of a gag protein, said core itself surrounding (iii) genome components, usually constituted of ribonucleic acids (RNA), and (iv) an enzyme component (pol). The biological material can be present within the envelope, within the core and/or within the genome components.

Lentiviral vector particles can be readily prepared by the skilled person, for example by following the general guidance provided by Sandrin et al. (2002) *Blood* 100:823-832. Briefly, the lentiviral vector particles may be generated by co-expressing the packaging elements (i.e. the core and enzyme components), the genome component and the envelope component in a so-called producer cell, e.g. 293T human embryonic kidney cells. Typically from three to four plasmids may be employed, but the number may be greater depending upon the degree to which the lentiviral components are broken up into separate units.

As used herein, the term "pseudotyped viral vector" refers to a viral vector comprising foreign viral envelope glycoproteins. Typically, the viral vectors according to the invention are pseudotyped with the above defined chimeric or modified glycoproteins.

The Baboon endogenous retrovirus or BaEV is a type C retrovirus present in multiple proviral copies in the DNA of baboons. The BaEV envelope glycoprotein is notably described in Benveniste et al. (1974) *Nature* 248:17-20 and Todaro et al. (1974) *Cell* 2:55-61.

In the context of the invention, the term "BaEV envelope glycoprotein" refers to the wild-type form of the BaEV envelope glycoprotein or to a mutant of said wild-type BaEV envelope glycoprotein which is at least 80%, preferably at least 85%, still preferably at least 90%, more preferably at least 95%, still more preferably at least 99% identical to said wild-type BaEV envelope glycoprotein, provided that said mutant glycoprotein retains the capacity of the wild-type glycoprotein of binding to and fusing with hematopoietic cells membrane.

Typically, the wild-type BaEV envelope glycoprotein is encoded by the nucleic acid sequence SEQ ID NO: 1. Preferably, it consists of the sequence SEQ ID NO: 2. As known from the skilled person, the BaEV envelope glycoprotein is constituted by a cytoplasmic tail domain, a transmembrane domain and an extracellular domain. The regions corresponding to the cytoplasmic tail domain, the transmembrane domain and extracellular domain in the envelope glycoprotein sequence can be easily determined by the skilled person. Typically, the cytoplasmic tail domain is located between amino acids 530 to 564 of the wild-type BaEV envelope glycoprotein. Preferably, the wild-type cytoplasmic tail domain of the BaEV envelope glycoprotein comprises or consists in the amino acid sequence SEQ ID NO: 3. Typically, the transmembrane domain is located between amino acids 507 to 529 of the wild-type BaEV envelope glycoprotein. Preferably, the wild-type transmembrane domain of the BaEV envelope glycoprotein comprises or consists in the amino acid sequence SEQ ID NO: 4. Typically, the extracellular domain is located between amino acids 1 to 506 of the wild-type BaEV envelope glycoprotein. Preferably, the wild-type extracellular domain of the BaEV envelope glycoprotein comprises or consists in the amino acid sequence SEQ ID NO: 5.

In a particular embodiment of the invention, the cytoplasmic tail domain of the BaEV envelope glycoprotein is devoid of the fusion inhibitory R peptide.

In the context of the invention, the expression "fusion inhibitory R peptide" refers to the C-terminal portion of the cytoplasmic tail domain of the envelope glycoprotein which harbours a tyrosine endocytosis signal—YXXL—and which is cleaved by viral protease during virion maturation, thus enhancing membrane fusion of the envelope glycoprotein. The fusion inhibitory R peptide of the BaEV envelope glycoprotein is typically located between amino acids 547 and 564 of the wild-type BaEV envelope glycoprotein. Preferably, the fusion inhibitory R peptide of the BaEV envelope glycoprotein comprises or consists in the amino acid sequence SEQ ID NO: 6.

Therefore, in a particularly preferred embodiment, the modified BaEV envelope glycoprotein wherein the cytoplasmic tail domain is devoid of the fusion inhibitory R peptide comprises or consists in the amino acid sequence SEQ ID NO: 7. Such a modified BaEV envelope glycoprotein is called herein after "BaEVRLess".

In another particular embodiment, the cytoplasmic tail domain of the BaEV envelope glycoprotein is replaced by the cytoplasmic tail domain of a murine leukemia virus (MLV) envelope glycoprotein.

The Murine Leukemia Virus envelope glycoprotein is notably described in Ott et al. (1990) *J. Virol.* 64:757-766. The Murine Leukemia Virus envelope glycoprotein is preferably that of strain 4070A.

In the context of the invention, the term "MLV envelope glycoprotein" refers to the wild-type form of the MLV envelope glycoprotein or to a mutant of said wild-type MLV envelope glycoprotein which is at least 80%, preferably at least 85%, still preferably at least 90%, more preferably at least 95%, still more preferably at least 99% identical to said wild-type MLV envelope glycoprotein, provided that said mutant glycoprotein retains the capacity of the wild-type envelope glycoprotein of interacting with viral core proteins, in particular with lentiviral core proteins.

The region corresponding to the cytoplasmic tail domain in the envelope glycoprotein sequence can be easily determined by the skilled person. Typically, the cytoplasmic tail domain of the MLV envelope glycoprotein is located between amino acids 622 and 654 of the wild-type MLV envelope glycoprotein. Preferably, the wild-type cytoplasmic tail domain of the MLV envelope glycoprotein comprises or consists in the amino acid sequence SEQ ID NO: 8.

Therefore, in a particularly preferred embodiment, the chimeric envelope glycoprotein which comprises or consists in a fusion of the transmembrane and extracellular domain of a BaEV envelope glycoprotein and the cytoplasmic tail domain of a MLV envelope glycoprotein comprises or consists in the amino acid sequence SEQ ID NO: 9. Such a chimeric envelope glycoprotein is called herein after "BaEV/TR".

The inventors demonstrated that BaEV/TR and BaEVRLess glycoproteins were incorporated at a higher level on the lentiviral surface than the wild-type BaEV glycoprotein.

The inventors further demonstrated that the co-display of specific cytokines on the viral vector particles enabled enhancing the targeted transduction of cells of interest.

Therefore, in a particular embodiment, the viral vector particle according to the invention may further display, preferably at its surface, at least one cytokine selected from the group consisting of stem cell factor (SCF), thrombopoietin (TPO), IL-2, IL-15 and IL-7.

Preferably, said at least one cytokine is selected from the group consisting of human SCF, human TPO, human IL-2, human IL-15 and human IL-7.

In the context of the invention, the cytokine may be a wild-type cytokine or any mutant of said wild-type cytokine which is at least 80%, preferably at least 85%, still preferably at least 90%, more preferably at least 95%, still more preferably at least 99% identical to said wild-type cytokine, provided that said mutant cytokine presents essentially the same properties as the wild-type cytokine from which it derives.

The wild-type SCF cytokine preferably comprises or consists in the sequence SEQ ID NO: 10. The wild-type TPO preferably comprises or consists in the sequence SEQ ID NO: 11. The wild-type IL-2 preferably comprises or consists in the sequence SEQ ID NO: 12. The wild-type IL-7 preferably comprises or consists in the sequence SEQ ID NO: 13. The wild-type IL-15 preferably comprises or consists in the sequence SEQ ID NO: 14.

The percentage of identity may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

In a particularly preferred embodiment, the pseudotyped viral vector particle according to the invention is obtainable or obtained by the method of production described in the section "Method for producing a pseudotyped viral vector particle" herein below.

Biological Material

The pseudotyped viral vector particles of the invention are of particular interest for transferring biological materials into cells, in particular into hematopoietic cells.

Accordingly, in a preferred embodiment, the pseudotyped viral vector particles as defined above further comprise a biological material.

As intended herein the expression "biological material" relates to one or more compounds liable to alter the structure and/or the function of a cell. Within the context of the present invention, it is preferred that the biological material is one or more nucleic acids, which in the case of lentiviral vector particles may be comprised within the genome of the vector particle. The genome typically comprises the one or more nucleic acids, preferably linked to genetic elements necessary for their expression in the target cell, such as promoters and terminators, flanked by cis-acting elements necessary for the inclusion of the genome in the core element, its reverse transcription into deoxyribonucleic acid (DNA), the import of the retrotranscribed genome into the nucleus of the target cell and the integration of the retrotranscribed genome within the genome of the target cell.

Examples of nucleic acids of interest include globin genes, hematopoietic growth factors, which include erythropoietin (EPO), the interleukins (especially Interleukin-1, Interleukin-2, Interleukin-3, Interleukin-6, Interleukin-12, etc.) and the colony-stimulating factors (such as granulocyte colony-stimulating factor, granulocyte/macrophage colony-stimulating factor, or stem-cell colony-stimulating factor), the platelet-specific integrin αIIbβ, multidrug resistance genes, the gp91 or gp 47 genes which are defective in patients with chronic granulomatous disease (CGD), antiviral genes rendering cells resistant to infections with pathogens such as human immunodeficiency virus, genes coding for blood coagulation factors VIII or IX which are mutated in hemophilia's, ligands involved in T cell-mediated immune responses such as T cell antigen receptors, B cell antigen receptors (immunoglobulins), the interleukin receptor common γ chain, a combination of both T and B cell antigen receptors alone and/or in combination with single chain antibodies (ScFv), IL2, IL12, TNF, gamma interferon, CTLA4, B7 and the like, genes expressed in tumor cells such as Melana, MAGE genes (such as MAGE-1, MAGE-3), P198, P1A, gp100 etc.

As intended herein "transferring" relates to the capacity of the vector particle to initially deliver the biological material to the membrane or the cytoplasm of the target cell, upon being bound to the target cell. After delivery, the biological material can be translocated to other compartment of the cell.

As intended herein the recipient cells for the biological material to be transferred, or target cells, relate to any cell liable to be bound by the above-defined vector particle. Where the vector particle is a lentiviral vector particle, the target cell relates to any cell liable to be transduced by the vector particle. These cells are preferably hematopoietic cells, in particular human hematopoietic cells.

Hematopoietic Cells

As used herein, the term "hematopoietic cell" refers generally to blood cells, both from the myeloid and the lymphoid lineage. In particular, the term "hematopoietic cell" includes both undifferentiated or poorly differentiated cells such as hematopoietic stem cells and progenitor cells, and differentiated cells such as T lymphocytes, B lymphocytes or dendritic cells. Preferably, the hematopoietic cell is selected from the group consisting of hematopoietic stem cells, $CD34^+$ progenitor cells, in particular peripheral blood $CD34^+$ cells, very early progenitor $CD34^+$ cells, B-cell $CD19^+$ progenitors, myeloid progenitor $CD13^+$ cells, T lymphocytes, B lymphocytes, monocytes, dendritic cells, cancer B cells in particular B-cell chronic lymphocytic leukemia (BOLL) cells and marginal zone lymphoma (MZL) B cells, and thymocytes.

As known from the skilled person, every hematopoietic cell is produced from bone marrow hematopoietic stem cells.

As used herein, the term "hematopoietic stem cell" or "HSC" refers to cells able to replenish all blood cell types and to self-renew. Hematopoietic stem cells may be in particular defined as cells that keep the levels of myeloid, T and B cells at robustly detectable levels (typically more than 1% of peripheral blood cells) for 16 weeks when injected into the circulation of a recipient mouse with a depleted hematopoietic system (Schroeder (2010) *Cell Stem Cell* 6:203-207).

As used herein, the term "$CD34^+$ progenitor cell" refers to a heterogeneous cell population that includes a subpopulation of HSCs, pluripotent stem cells and cells in the early stages of lineage commitment. $CD34^+$ progenitor cells continuously migrate to and from the bone marrow in normal adult animals. They can differentiate to produce all hematopoietic cell lineages found in the circulation. The expression "peripheral blood $CD34^+$ cell" refers more particularly to $CD34^+$ cells present in the blood.

The inventors prestimulated human $CD34^+$ early progenitor cells with a strong cytokine cocktail (SCF, TPO and Flt3-L) and transduced them BaEV/TR and BaEVRLess pseudotyped lentiviral vector particles. They demonstrated that the pseudotyped lentiviral vector particles could efficiently transduce human $CD34^+$ early progenitor cells, in particular at more than 70% in presence of retronectin.

The inventors further demonstrated that the high human $CD34^+$ cell transduction obtained with BaEV/TR and BaEVRLess pseudotyped lentiviral vector particles was due to stable transduction of short term progenitors. Indeed, there was no significant difference between the proportion of BaEV/TR and BaEVRLess lentiviral vector particles transduced $CD34^+$ cells after a SCF/TPO prestimulation and the clonogenic progenitors derived from them. In contrast, for lentiviral vector particles pseudotyped with VSV-G, the proportion of transduced clonogenic progenitors was significantly lower than the rate of transduced $CD34^+$ cells they were derived from.

As used herein, the term "very early progenitor $CD34^+$ cell" refers to a subgroup of $CD34^+$ progenitor cells which is enriched in HSCs.

As used herein, the term "B-cell $CD19^+$ progenitor" refers to a population of B-lineage cells that express cell surface CD10, CD34 and CD19.

As used herein, the term "myeloid progenitor $CD13^+$ cell" refers to a population of myeloid lineage cells that express cell surface CD34 and CD13 and optionally CD33.

The inventors demonstrated that BaEV/TR and BaEVRLess pseudotyped lentiviral vector particles were able to transduce at high efficiency hematopoietic progenitors capable of repopulating immunodeficient mice. They evaluated the long-term reconstitution capacity of these pseudotyped lentiviral vector particles transduced human $CD34^+$ cells in the $Rag2^{-/-}$ $\gamma^{-/-}$ Balbc immunodeficient mice model and the NOD/SCID/γc−/− (NSG) mice model. They demonstrated that very early progenitor $CD34^+$ cells, as well as B-cell $CD19^+$ progenitors and myeloid $CD13^+$ cells were transduced to the same extent by BaEV/TR and BaEVRLess pseudotyped lentiviral vector particles of the invention at low infectious vector particle doses. Moreover, BaEV/TR-LVs and BaEVRLess-LVs transduced hCD34+ cells resulted in high reconstitution levels in the bone marrow and the highest transduction levels of SCID repopulating cells (up to 90% CD45+GFP+ cells) in the bone marrow. They also demonstrated that these high transduction levels were sustained in the primary recipient mice in all hematopoietic tissues (bone marrow, thymus and spleen). Equivalent high level transduction was detected for immature progenitors (hCD34+ cells), lymphoid cells (CD19+) and myeloid cells (CD13+ and CD14+) in the bone marrow. On the contrary, lentiviral vector particles pseudotyped with VSV-G transduced early $CD34^+$ progenitors, $CD13^+$ myeloid progenitors and monocytes to much lower levels. For lentiviral vector particles pseudotyped with RD114/TR, also low transduction of all the different bone marrow cell lineages was detected. An identical picture was found for T- and B-cells and monocytes in the spleen. RD114/TR-LVs demonstrated variable transduction levels of SCID repopulating cells (ranging from 3.2-76% of GFP+ CD45+ cells).

The inventors also showed that in the spleen and bone marrow the percentage of GFP+ hCD45+ cells was maintained or increased after secondary engraftment of the $hCD34^+$ cells isolated from primary recipients in immunodeficient mice. Moreover, for both BaEV/TR- and BaEVRLess-LVs, high levels of GFP+ hCD34+ early progenitor, lymphoid (CD19+) and myeloid (CD13+) cells were detected in the bone marrow of these secondary recipient mice and equivalent percentages of GFP+ cells were detected in these different lineages. The inventors thus showed that the secondary reconstituting SCID repopulating cells were capable of multilineage differentiation and that true human HSC were genetically modified to high levels by BaEV/TR- and BaEVRLess-LVs.

The inventors also showed that BaEV/TR and BaEVRLess pseudotyped lentiviral vector particles allowed efficient transduction of human T cells, in particular of IL-7 prestimulated human T cells. These pseudotyped lentiviral vector particles were superior over lentiviral vector particles pseudotyped with VSV-G for the same vector doses in the presence of retronectin. Importantly, the BaEV/TR and BaEVRLess pseudotyped lentiviral vector particles allowed an efficient transduction of both naïve and memory IL-7 prestimulated T cells. Indeed, they allowed transduction of IL-7 stimulated T-cells without compromising their naive phenotype. Of high interest, they also permitted close to 100% T cell gene transfer upon T-cell receptor (TCR) stimulation at an MOI of 10.

Therefore, in a particular embodiment, the targeted hematopoietic cell is a T cell, preferably a naive or a memory T cell.

The BaEV/TR and BaEVRLess pseudotyped lentiviral vector particles also permitted highly efficient transduction of 20-30% of resting B cells and thus outperformed by far the lentiviral vector particles pseudotyped with VSV-G or RD114/TR which enabled no transduction or very low transduction of resting human B cells. Furthermore, upon B cell receptor (BCR) stimulation, BaEV/TR and BaEVRLess pseudotyped lentiviral vector particles transduced up to 70% of the B cells while lentiviral vector particles pseudotyped with VSV-G transduction efficiency did not exceed 5%. Of importance, as well memory as naïve B cells were efficiently transduced by BaEV/TR and BaEVRLess pseudotyped lentiviral vector particles.

Therefore, in a particular embodiment, the targeted hematopoietic cell is a B cell, in particular a resting B cell, preferably a naive or a memory B cell. It may also be a cancer B cell, in particular a B-cell chronic lymphocytic leukemia (BOLL) cell or a marginal zone lymphoma (MZL) B cell.

Because of the potential value of thymocyte gene transfer for immune modulation, the inventors evaluated the performance of BaEVgp-LVs compared to the other LV pseudotypes for the transduction of different thymocyte subpopulations. Upon isolation of thymocytes from a human thymus, they transduced them in the presence of the survival cytokine IL-7 with VSV-G-, RD114/TR-, BaEV/TR-, and BaEVRLess-LVs encoding for the GFP reporter at an MOI of 10. The inventors showed that RD114/TR-LV, BaEV/TR-LVs and BaEVRLess-LVs allow preferential transduction of the thymocytes in the early stages of development (double negative and immature CD4 single positive cells) while they still transduce the more mature to a lower level. As already detected for adult human T cells, BaEVgp LVs transduced all different thymocyte subpopulations more efficiently than the RD114/TR-LVs. Moreover, transduction with the different lentiviral vector pseudotypes had no effect on the distribution of different thymocyte subpopulations. The inventors thus demonstrated that BaEVgp-LVs are excellent tools for transduction of thymocytes and that they are especially superior over VSV-G- and RD114/TR-LVs for the transduction of the immature double negative (DN) and immature CD4 single positive cells (ISP) thymocyte subpopulations.

Therefore, in a particular embodiment, the targeted hematopoietic cell is a thymocyte.

Finally, the inventors prestimulated freshly isolated total CB T cells with the T cell survivial cytokine IL-7 to conserve the T cell naive phenotype, and subsequently transduced them with the different vectors: VSV-G-, RD114/TR-, BaEV/TR-, and BaEVRLess-LVs encoding the GFP reporter at an MOI of 10 or 20, or at an MOI of 50 for VSV-G-LVs. They showed that BaEV/TR- and BaEVRLess-LVs present a transduction efficiency highly superior (40-50% transduction) at an MOI=10 as compared to VSV-G or RD114/TR-LVs. Importantly, BaEV/TR- and BaEVRLess-LVs reached easily 65% transduction when the vector dose was 2-fold increased (MOI=20). In all cases the naive recent thymocyte emigrants (CD69L+ CD45RA+ CD31+) were transduced to the same extent as the more mature naive CB T cells (CD69L+ CD45RA+ CD31−). Moreover, transduction had no effect on the distribution of these two naive CB T cell populations.

Therefore, in a particular embodiment, the targeted hematopoietic cell is a naïve cell. As used herein, the term "naïve cell" refers to a cell that has not yet undergone cell activation in response to a stimulus. In particular, a "naïve cell" may be a cell that has not yet been exposed to an antigen.

Since a strong stimulation with a cytokine cocktail induces HSC differentiation and their loss of self renewal capacity, it is of particular interest to prestimulate the cells as less as possible, to avoid their differentiation as much as possible and to keep the more their "stem-cell features".

The inventors applied the pseudotyped viral vectors of the invention at a fixed MOI (number of infectious particles per cell) of 10 and different cytokine prestimulation protocols on human $CD34^+$ early progenitor cells: 1) no stimulation; 2) stimulation with a SCF or TPO; 3) stimulation with SCF and TPO; 4) stimulation with SCF, TPO and Flt3-L. Important, the strongest cytokine prestimulation cocktail used was lower than prestimulation cocktails currently used in clinical setting with the objective to limit cell differentiation. The inventors demonstrated that BaEV/TR and BaEVRLess lentiviral vector particles were able to transduce 10-20% of unstimulated human $CD34^+$ early progenitor cells, whereas lentiviral vectors pseudotyped with VSV-G or RD114/TR (as described in international application WO2009/013324) were unable to transduce unstimulated quiescent human $CD34^+$ early progenitor cells efficiently at the same vector doses. Furthermore a single TPO stimulation was sufficient for a transduction of human $CD34^+$ early progenitor cells of up to 60% for BaEV/TR and BaEVRLess pseudotyped lentiviral vectors, while lentiviral vectors pseudotyped with VSV-G or RD114/TR only transduced 8 to 20% of human $CD34^+$ early progenitor cells under these conditions. SCF single prestimulation permitted up to 30-50% of transduction of human $CD34^+$ early progenitor cells with BaEV/TR and BaEVRLess pseudotyped lentiviral vectors, whereas lentiviral vectors pseudotyped with VSV-G or RD114/TR only reached transduction levels of 10% Finally, a combination of TPO and SCF or of TPO, SCF and Flt3-L prestimulation with a single BaEV/TR or BaEVRLess pseudotyped lentiviral vector incubation resulted in up to 75% transduction of human $CD34^+$ early progenitor cells, while lentiviral vectors pseudotyped with RD114/TR only achieved 40% of transduction.

Accordingly, in a preferred embodiment, the targeted hematopoietic cell is not prestimulated with at least one cytokine. In particular it is not prestimulated with SCF, TPO and/or Flt3-L.

In another preferred embodiment, the targeted hematopoietic cell is only prestimulated with SCF or TPO. In still another preferred embodiment, the targeted hematopoietic cell is only prestimulated with SCF and TPO.

As used herein, the term "prestimulation" or "prestimulated" means that the hematopoietic cell is contacted with at least one cytokine at a concentration or for a period suitable to induce a specific activation of the hematopoietic cell.

As used herein, the term "fms-like tyrosine kinase receptor-3 ligand", "Flt3 ligand" or "Flt3-L" refers to a cytokine that increases the number of immune cells by activating the hematopoietic progenitors. Flt3-L is preferably human Flt3-L and more preferably comprises or consists in the sequence SEQ ID NO: 15.

Method for Producing a Pseudotyped Viral Vector Particle

The present invention also relates to a method for producing a pseudotyped viral vector particle comprising:
  a) transfecting a cell with:
    (i) at least one first nucleic acid sequence comprising a packaging competent retroviral derived genome;

(ii) at least one second nucleic acid sequence comprising a cDNA encoding core proteins from said retrovirus, and
(iii) at least one third nucleic acid sequence comprising a cDNA encoding:
   a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein, as defined above; or
   a modified BaEV envelope glycoprotein wherein the cytoplasmic tail domain is devoid of the fusion inhibitory R peptide, as defined above;
   to yield a producer cell;
b) maintaining the producer cell in culture for sufficient time to allow expression of the cDNAs to produce the encoded proteins; and
c) allowing the encoded proteins to form viral vector particles of the invention.

By "retrovirus" is meant a virus whose genome consists of a RNA molecule and that comprises a reverse-transcriptase, i.e. a member of the Retroviridae family. Retroviruses are divided into Oncovirus, Lentivirus and Spumavirus. Preferably said retrovirus is an oncovirus, e.g. MLV, ALV, RSV, or MPMV, a lentivirus, e.g. HIV-1, HIV-2, SIV, EIAV, or CAEV, or a spumavirus such as HFV. Genomes of these retroviruses are readily available in databanks. More preferably said retrovirus is a lentivirus, in particular HIV-1, HIV-2 or SIV.

In the context of the invention "a nucleic sequence comprising a packaging competent retrovirus-derived genome" is intended for a sequence that comprises the retroviral nucleic acid sequences known as "cis-acting" sequences. These include the Long Terminal Repeats (LTRs) for the control of transcription and integration, the psi sequence necessary for encapsidation, and the Primer Binding site (PBS) and polypurine track (PPT) sequences necessary for reverse transcription of the retroviral genome. Advantageously, said nucleic acid sequence comprising a packaging competent retrovirus-derived genome further comprises a transgene.

Said retroviral genome may be replication-defective or replication-competent, in the absence of any trans-complementing function. A replication-competent genome would further comprise the gag, pol, and env retroviral genes. In a replication-defective genome, the viral genes gag, pol, and env are deleted. However, assembly of the viral vector particles of the invention may be achieved by providing in trans another plasmid that encodes gag, pol and/or env glycoprotein but that is defective for the "cis" sequences. Their expression allows the encapsidation of the transgene, excluding the genes necessary for the multiplication of the viral genome and for the formation of complete viral particles.

The "core protein from a retrovirus" refers to proteins encoded by the gag and pol genes. The gag gene encodes a polyprotein which is further processed by the retroviral protease into structural proteins that comprise the core. The pol gene encodes the retroviral protease, reverse-transcriptase, and integrase.

For the purpose of transfection, said first, second and third nucleic acid sequences may be carried on a same vector, or on two or three separated vectors. Generally, one plasmid encodes the core retroviral component of the viral vector particle. The origin of the gag and pol genes gives its name to the viral vector particle. For instance the expression "HIV-1-derived vector particle" usually indicates that the gag and pol genes of the vector particle are those of HIV-1.

The term "transfection" means the introduction of a foreign nucleic acid (DNA, cDNA or RNA) into a cell so that the host cell will express the introduced gene or sequence to produce a desired substance, typically a protein coded by the introduced gene or sequence. The introduced gene may include regulatory or control sequences, such as start, stop, promoter, signal, secretion, or other sequences used by a cell's genetic machinery. A host cell that receives and expresses introduced DNA or RNA has been "transfected".

For the production of vector particles, one may employ any cell that is compatible with the expression of lentiviral Gag and Pol genes, or any cell that can be engineered to support such expression. For example, producer cells such as 293T cells and insect cells (in particular for HIV derived vectors), TE 671 and HT1080 cells (in particular for MLV derived vectors) may be used.

Therapeutical Applications

The present invention also relates to a medicament comprising a pseudotyped viral vector particle as defined above as active ingredient, in particular a pseudotyped viral vector particle as defined above further comprising a biological material which is preferably one or more nucleic acids.

It also relates to a pharmaceutical composition comprising a pseudotyped viral vector particle as defined above, in particular a pseudotyped viral vector particle as defined above further comprising a biological material which is preferably one or more nucleic acids, and a pharmaceutically acceptable carrier.

The present invention also concerns a method for treating a subject in need thereof comprising administering a therapeutically effective amount of a pseudotyped viral vector particle as defined above, in particular a pseudotyped viral vector particle as defined above further comprising a biological material which is preferably one or more nucleic acids, to the subject in need thereof.

In the context of the present invention, a "subject" denotes a human or non-human mammal, such as a rodent (rat, mouse, rabbit), a primate (chimpanzee), a feline (cat), a canine (dog). Preferably, the subject is human.

As used herein, the term "pharmaceutically acceptable carrier" refers to a carrier that may be administered to a patient, together with a viral vector of this invention, and does not destroy the pharmacological activity thereof and is non-toxic when administered in doses sufficient to deliver a pharmaceutically effective amount of the viral vector.

Pharmaceutically acceptable carriers and vehicles that may be used in the pharmaceutical compositions of this invention include, but are not limited to, ion exchangers, alumina, aluminium stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compositions according to the invention.

Any suitable method of administration known from one skilled in the art may be used. In particular, the pseudotyped viral vector particle according to the invention may be administered for example by the oral route or by the parenteral route (in particular by intravenous injection and intra-femur (bone marrow cavity) injection). When the parenteral route is selected, the pseudotyped viral vector particles may be in the form of injectable solutions and suspensions, conditioned in ampoules or flasks. The forms for parenteral delivery are conventionally obtained by mixing the pseudotyped viral vector particles according to the invention with buffers, stabilizers, preservatives, solubilizing agents, isotonic agents and slurrying agents. According to known techniques, these mixtures can then be sterilized and conditioned in the form of intravenous injections. One of skill in the art may use organic phosphate salts-based buffers as buffer. Examples of slurrying agents include methylcellulose, acacia and sodium carboxymethylcellulose. Examples of stabilizers include sodium sulphite and sodium metasulphite, and examples of preservatives include sodium p-hydroxybenzoate, sorbic acid, cresol and chlorocresol.

A "therapeutically effective amount" refers to a quantity of a viral vector that confers a therapeutic effect on the treated subject. The therapeutic effect may be objective (i.e., measurable by some test or marker) or subjective (i.e., subject gives an indication of or feels an effect). As known from the skilled person, effective doses will vary depending on route of administration, the size and/or weight of the subject, as well as the possibility of co-usage with other agents.

Where the pseudotyped viral vector particle is used as a medicament and is administered to a subject in a therapeutic method, administration through the intravenous route or by the medullar route, in particular the femur or humerus medullar route, is preferred. For intravenous administration a unit dose from about $5 \cdot 10^8$ to about $10^9$ pseudotyped viral vector particles as defined above can be used, whereas for medullar administration a unit dose from about $10^8$ to about $5 \cdot 10^8$ pseudotyped viral vector particles as defined above can be used.

In a particular embodiment, the pseudotyped viral vector particle of the invention is for use in the treatment of a hematopoietic disorder or an autoimmune disease.

The present invention also relates to the use of a pseudotyped viral vector particle as defined above for the manufacture of medicament intended for the treatment of a hematopoietic disorder or an autoimmune disease. It also relates to a method for treating a hematopoietic disorder or an autoimmune disease, in a subject comprising administering a therapeutically efficient amount of a pseudotyped viral vector particle of the invention in a subject in need thereof.

As used herein, the expression "hematopoietic disorder" refers to a blood disease, in particular a disease involving hematopoietic cells. Preferably, said hematopoietic disorder is a monogenic hematopoietic disease.

As used herein, the expression "monogenic hematopoietic disease" refers to a genetic hematopoietic disease, which is due to the mutation of a single gene.

Examples of hematopoietic disorders include myelodysplasia, aplastic anemia, Fanconi anemia, paroxysmal nocturnal hemoglobinuria, Sickle cell disease, Diamond Blackfan anemia, Schachman Diamond disorder, Kostmann's syndrome, chronic granulomatous disease, adrenoleukodystrophy, leukocyte adhesion deficiency, hemophilia, thalassemia, beta-thalassemia, leukaemia such as acute lymphocytic leukemia (ALL), acute myelogenous (myeloid) leukemia (AML), adult lymphoblastic leukaemia, chronic lymphocytic leukemia (CLL), B-cell chronic lymphocytic leukemia (B-CLL), chronic myeloid leukemia (CML), juvenile chronic myelogenous leukemia (CML), and juvenile myelomonocytic leukemia (JMML), severe combined immunodeficiency disease (SCID), X-linked severe combined immunodeficiency, Wiskott-Aldrich syndrome (WAS), adenosine-deaminase (ADA) deficiency, chronic granulomatous disease, Chediak-Higashi syndrome, Hodgkin's lymphoma, non-Hodgkin's lymphoma (NHL) and AIDS.

Preferably, the hematopoietic disorder is selected from the group consisting of Fanconi anemia, hemophilia, beta-thallasemia, Wiskott-Aldrich syndrome, X-linked severe combined immunodeficiency, adenosine-deaminase deficiency, chronic granulomatous disease and adrenoleukodystrophy.

As used herein, the expression "autoimmune disease" refers to a disease due to an overactive immune response of the body against substances and tissues normally present in the body. Accordingly, by specifically targeting immune (hematopoietic) cells involved in this overactive immune response, the vector particles of the invention could be useful tools in the treatment of autoimmune diseases.

Autoimmune diseases include in particular acute disseminated encephalomyelitis, acute hemorrhagic leukoencephalitis, Addison's disease, Agammaglobulinemia, Alopecia areata, amyotrophic lateral sclerosis, ankylosing spondylitis, antiphospholipid syndrome, antisynthetase syndrome, atopic allergy, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease, Balo concentric sclerosis, Bechets syndrome, Berger's disease, Bickerstaff's encephalitis, Blau syndrome, bullous pemphigoid, cancer, Castleman's disease, celiac disease, chronic inflammatory demyelinating polyneuropathy, chronic recurrent multifocal osteomyelitis, Churg-Strauss syndrome, cicatricial pemphigoid, Cogan syndrome, cold agglutinin disease, complement component 2 deficiency, cranial arteritis, CREST syndrome, Crohn's disease, Cushing's syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, discoid lupus erythematosus, eczema, enthesitis-related arthritis, eosinophilic fasciitis, eosinophilic gastroenteritis, epidermolysis bullosa acquisita, erythema nodosum, essential mixed cryoglobulinemia, Evan's syndrome, firodysplasia ossificans progressiva, fibrosing aveolitis, gastritis, gastrointestinal pemphigoid, giant cell arteritis, glomerulonephritis, goodpasture's syndrome, Grave's disease, Guillain-Barré syndrome (GBS), Hashimoto's encephalitis, Hashimoto's thyroiditis, hemolytic anaemia, Henoch-Schonlein purpura, herpes gestationis, hypogammaglobulinemia, idiopathic inflammatory demyelinating disease, idiopathic pulmonary fibrosis, idiopathic thrombocytopenic purpura, IgA nephropathy, inclusion body myositis, inflammatory demyelinating polyneuropathy, interstitial cystitis, juvenile idiopathic arthritis, juvenile rheumatoid arthritis, Kawasaki's disease, Lambert-Eaton myasthenic syndrome, leukocytoclastic vasculitis, lichen planus, lichen sclerosus, linear IgA disease (LAD), Lou Gehrig's disease, lupoid hepatitis, lupus erythematosus, Majeed syndrome, Ménière's disease, microscopic polyangiitis, Miller-Fisher syndrome, mixed connective tissue disease, morphea, Mucha-Habermann disease, multiple sclerosis, myasthenia gravis, myositis, neuropyelitis optica, neuromyotonia, ocular cicatricial pemphigoid, opsoclonus myoclonus syndrome, ord thyroiditis, palindromic rheumatism, paraneoplastic cerebellar degeneration, paroxysmal nocturnal hemoglobinuria (PNH), Parry Romberg syndrome, Parsonnage-Turner syndrome, pars planitis, pemphigus, pemphigus vulgaris, permicious anemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatoid fever, sarcoidosis, Schmidt syndrome, Schnitzler syndrome, scleritis, scleroderma, Sjögren's syndrome, spondylarthropathy, Still's disease, stiff person syndrome, subacute bacterial endocarditis, Susac's syndrome, Sweet's syndrome, Sydenham chorea, sympathetic ophthalmia, Takayasu's arteritis, temporal arteritis, Tolosa-Hunt syndrome, transverse myelitis, ulcerative colitis, undifferentiated connective tissue disease, undifferentiated spondylarthropathy, vasculitis, vitiligo and Wegener's granulomatosis.

Preferably, the autoimmune disease is selected from cancer, diabetes, hemophilia, uveitis and encephalomyelitis.

As used herein, the term "cancer" encompasses any type of cancer but preferably includes cancers arising from hematopoietic cells, including leukemia, in particular B-CLL, CML or T cell based leukemia such as ALT, as well as melanoma.

Transducing Methods

The present invention also relates to the use of a pseudotyped viral vector particle as defined above, for transferring a biological material as defined in the section "Biological material" above, into hematopoietic cells as defined in the section "Hematopoietic cells" above, ex vivo.

Another object of the invention concerns a method for transducing a hematopoietic cell as defined in the section "Hematopoietic cells" above, comprising contacting the hematopoietic cell with a pseudotyped viral vector particle as defined above under conditions to effect the transduction of the hematopoietic cell by the pseudotyped viral vector particle.

As intended herein "transferring" or "transducing" relates to the capacity of the viral vector particle to initially deliver the biological material to the membrane or the cytoplasm of the target cell, upon being bound to the target cell. After delivery, the biological material can be translocated to other compartment of the cell.

Conditions to effect the transduction of the targeted cells are well-known from the skilled person and include typically incubating the cells to be transduced, preferably cultured in flasks, plates or dishes coated with retronectin, and optionally prestimulated with cytokine cocktails, with the pseudotyped viral vector particles of the invention, preferably at an MOI of 1, 5, 10 or 100, preferably in serum-free medium.

Packaging Cell Line

The invention also concerns a stable virus packaging cell line producing the pseudotyped viral vector particle as defined above, preferable producing the pseudotyped viral vector particle comprises at least a chimeric envelope glycoprotein which comprises or consists in a fusion of the transmembrane and extracellular domain of a BaEV envelope glycoprotein and the cytoplasmic tail domain of a MLV envelope glycoprotein.

Indeed, the inventors demonstrated that the BaEV/TR glycoprotein was not cytotoxic to the 293T producer cells.

In the context of the invention, a stable virus packaging cell line refers to a cell line which stably expresses the different components of the pseudotyped viral vector particle of the invention. Typically, the nucleic acids encoding the different components of the pseudotyped viral vector particle of the invention are integrated in the genome of the cell line.

In particular such stable virus packaging cell line may be any cell that is compatible with the expression of lentiviral Gag and Pol genes, or any cell that can be engineered to support such expression. For example, they can be 293T cells, and insect cells (in particular for HIV derived vectors), TE 671 and HT1080 cells (in particular for MLV derived vectors) may be used.

The present invention will be further illustrated by the following figures and example.

(and 100 for VSV-G pseudotyped lentiviral vector particles). Analysis of GFP expressing cells was performed 6 days after transduction by FACS.

Figure 6:
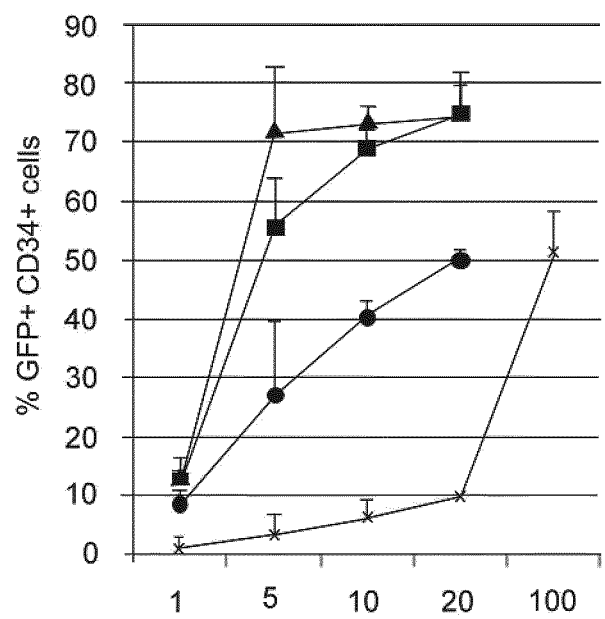

FIG. 6 shows graphs representing the percentage of transduction of SCF+TPO+Flt3-L prestimulated CD34+ cells by VSV-G (×), RD114/TR (●), BaEV/TR (▲) or BaEVRLess (■) pseudotyped lentiviral vector particles at MOIs of 1, 5, 10, 20 (and 100 for VSV-G pseudotyped lentiviral vector particles). Analysis of GFP expressing cells was performed 6 days after transduction by FACS.

Figure 7:
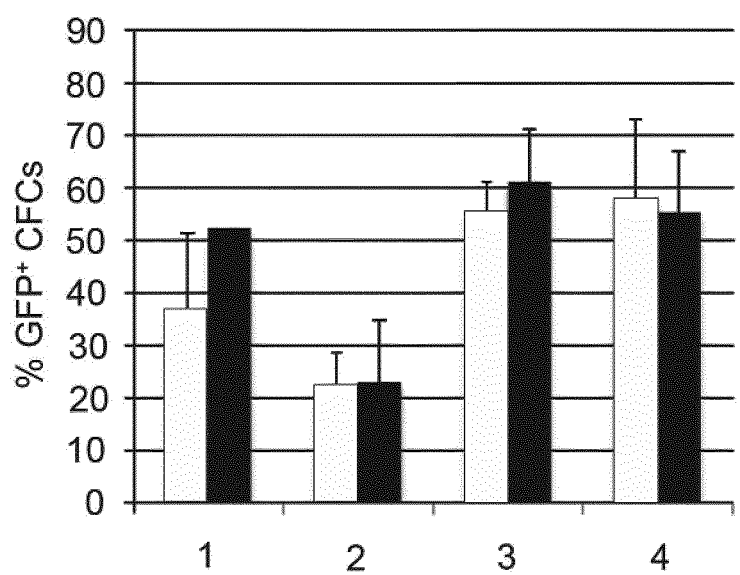

FIG. 7 shows histograms representing the percentage of erythrocyte, granulocyte and dendritic colony forming cells (CFCs) expressing GFP after transduction of SCF+TPO prestimulated (white bars) or SCF+TPO+Flt3-L prestimulated (black bars) cord blood-derived CD34+ cells by VSV-G (1), RD114/TR (2), BaEV/TR (3) or BaEVRLess (4) pseudotyped lentiviral vector particles at MOI of 100 for VSV-G and 10 for other pseudotypes. 3 days after transduction the cells were seeded in a medium supplied with cytokines to induce myeloid differentiation. On day 14 of culture erythrocyte, granulocyte and dendritic colony forming cells (CFCs) were scored for GFP expression by fluorescence microscopy after seeding.

Figure 8:
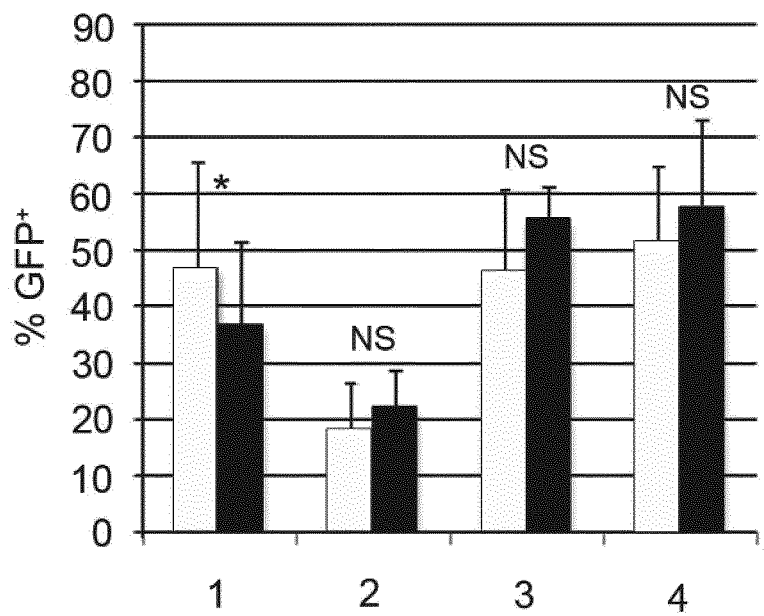

FIG. 8 shows histograms representing the percentage of erythrocyte, granulocyte and dendritic colony forming cells (CFCs) expressing GFP (black bars) and of CD34+ cells expressing GFP (white bars) after transduction of SCF+TPO prestimulated cord blood-derived CD34+ cells by VSV-G (1), RD114/TR (2), BaEV/TR (3) or BaEVRLess (4) pseudotyped lentiviral vector particles at MOI of 100 for VSV-G and 10 for other pseudotypes. 3 days after transduction the cells were seeded in a medium supplied with cytokines to induce myeloid differentiation. The percentage of GFP+ CD34+ cells was determined by FACS analysis 6 days after transduction. The percentage of GFP CFCs was determined by FACS analysis 17 days after transduction. Asterisk indicates that the proportion of GFP+ CD34+ cells differs statistically from the proportion of GFP+ colonies transduced cells (Student's T test: *: $p<0.05$, NS: not significant).

Figure 9:
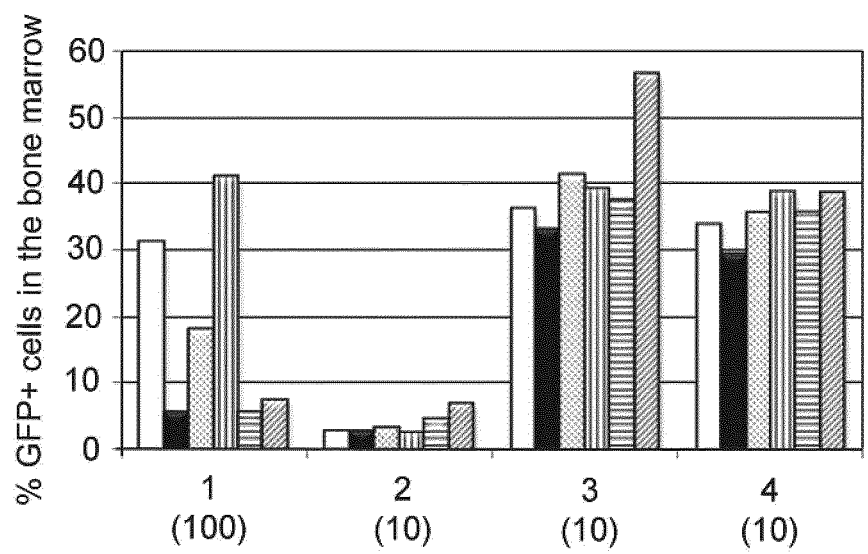

FIG. 9 shows histograms representing the percentage of CD45+ human cells (white bards), CD34+ CD19− immature progenitor cells (black bars), CD34+ CD19+ B progenitors (dashed bars), CD20+ B cells (vertical hatched bars), CD13+ myeloid progenitors (horizontal hatched bars), and CD14+ granulocytes and monocytes (diagonal hatched bars) in bone marrow expressing GFP after transduction of SCF+TPO prestimulated CD34+ cells for 48 hours with VSV-G (1), RD114/TR (2), BaEV/TR (3) and BaEVRLess (4) pseudotyped lentiviral vector particles at MOIs indicated into brackets. Upon irradiation of newborn Rag2$^{-/-}$; γc$^{-/-}$ Balbc mice, they were injected intrahepatically with 2·10$^5$ transduced human CD34+ cells. After 12 weeks of reconstitution, the mice were analyzed for human cell engraftment (CD45) in the bone marrow and the percentages of transduction (GFP+ cells) of different hematopoietic cell were analysed by FACS as indicated.

Figure 10:
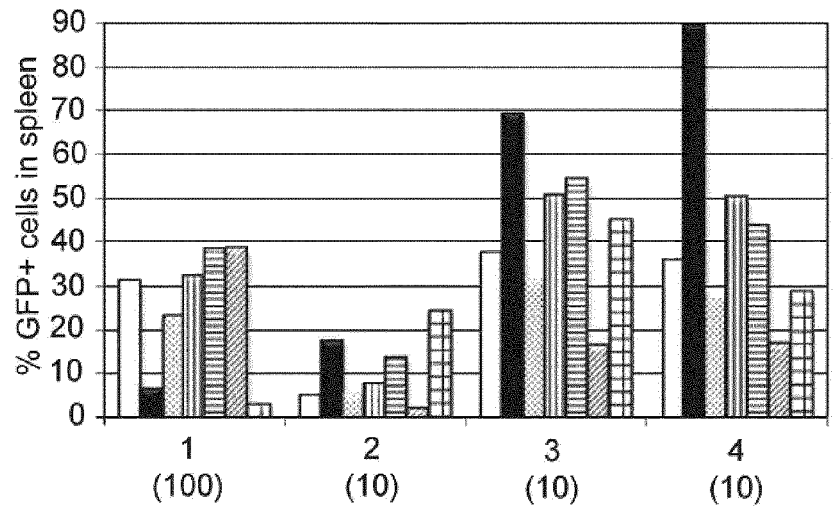

FIG. 10 shows histograms representing the percentage of CD45+ human cells (white bards), CD34+ CD10− CD19− very immature progenitor cells (black bars), CD34+ CD10+ CD19− B pre/pro B cells (dashed bars), CD19+ CD20− preB cells (vertical hatched bars), CD34+ CD10+ CD19+ immature B cells (horizontal hatched bars), CD20+ mature B cells (diagonal hatched bars) and CD3+ T cells (cross-hatched bars) in spleen expressing GFP after transduction of SCF/TPO prestimulated CD34+ cells for 48 hours with VSV-G, RD114/TR, BaEV/TR and BaEVRLess pseudotyped lentiviral vector particles at MOIs indicated into brackets. Upon irradiation of newborn Rag2$^{-/-}$; γc$^{-/-}$ Balbc mice, they were injected intrahepatically with 2·10$^5$ transduced human CD34+ cells. After 12 weeks of reconstitution, the mice were analyzed for human cell engraftment (CD45) in the spleen and the percentages of transduction (GFP+ cells) of different hematopoietic cell were analysed by FACS as indicated.

Figure 11:
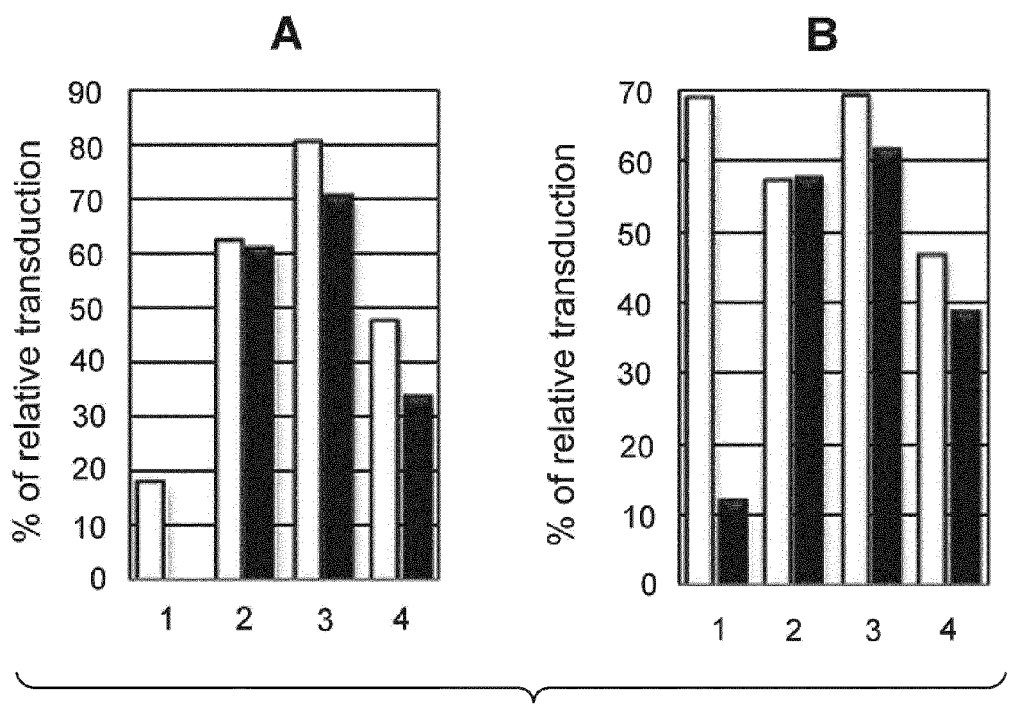

FIG. 11 shows histograms representing the relative percentage of transduction of macaques bone marrow CD34+ cells by VSV-G (1), RD114/TR (2), BaEV/TR (3) or BaEVRLess (4) pseudotyped SIV vector particles which were incubated at 37° C. for 1 hour in heat inactivated macaque sera (white bars; the serum was heat-inactivated at 56° C. before incubation with the vectors to inactivate the complement where fresh serum contains active complement) or in fresh macaque sera (black bars) relative to the transduction of the same virions incubated in FCS. The values of vector incubations with sera of 2 different macaques (A and B) are shown.

Figure 12:
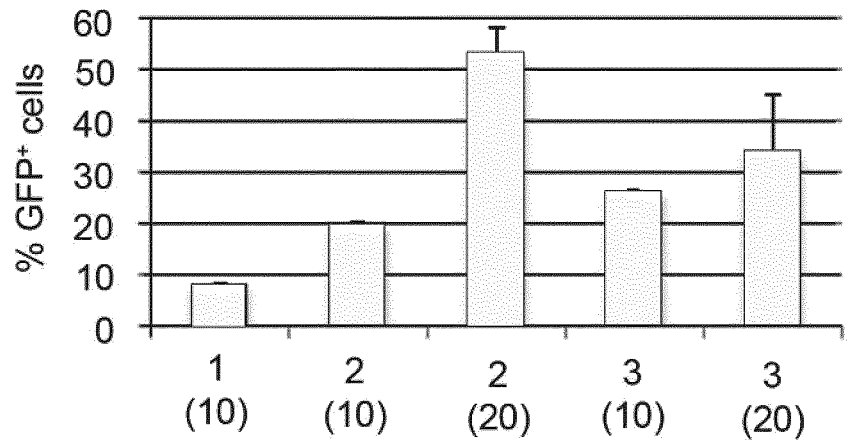

FIG. 12 shows histograms representing the percentage of SCF+Flt3-L+IL-3+IL-6 prestimulated cynomolgus macaque bone marrow CD34+ cells expressing GFP after transduction, in presence of retronectin, by VSV-G (1), BaEV/TR (2) or BaEVRLess (3) pseudotyped SIV vector particles at MOIs indicated into brackets.

Figure 13:
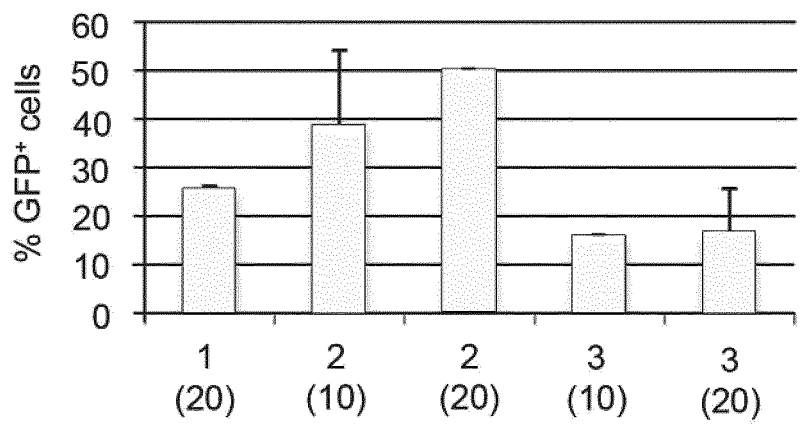

FIG. 13 shows histograms representing the percentage of SCF+Flt3-L+IL-3+IL-6 prestimulated rhesus macaque bone marrow CD34+ cells expressing GFP after transduction, in presence of retronectin, by VSV-G (1), BaEV/TR (2) or BaEVRLess (3) pseudotyped SIV vector particles at MOIs indicated into brackets.

Figure 14:
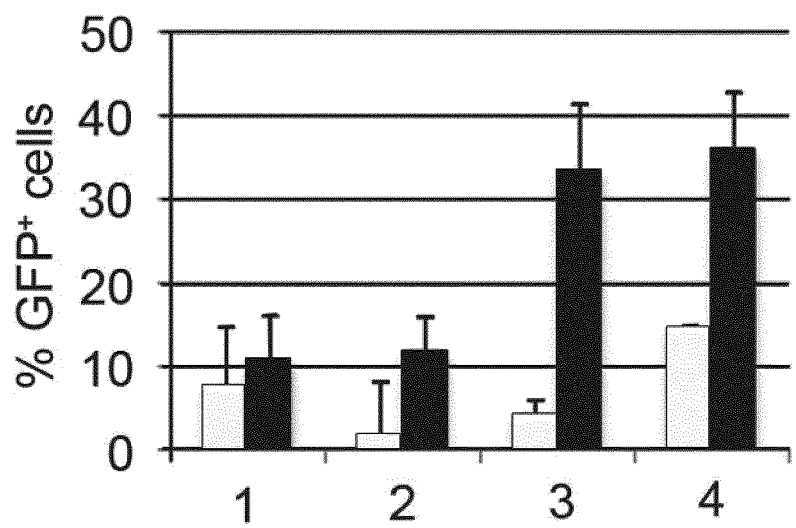

FIG. 14 shows histograms representing the percentage of IL-7 prestimulated T cells expressing GFP after transduction, in presence of retronectin (black bars) or not (white bars), by VSV-G (1), RD114/TR (2), BaEV/TR (3) or BaEVRLess (4) pseudotyped lentiviral vector particles at MOIs of 10.

Figure 15:
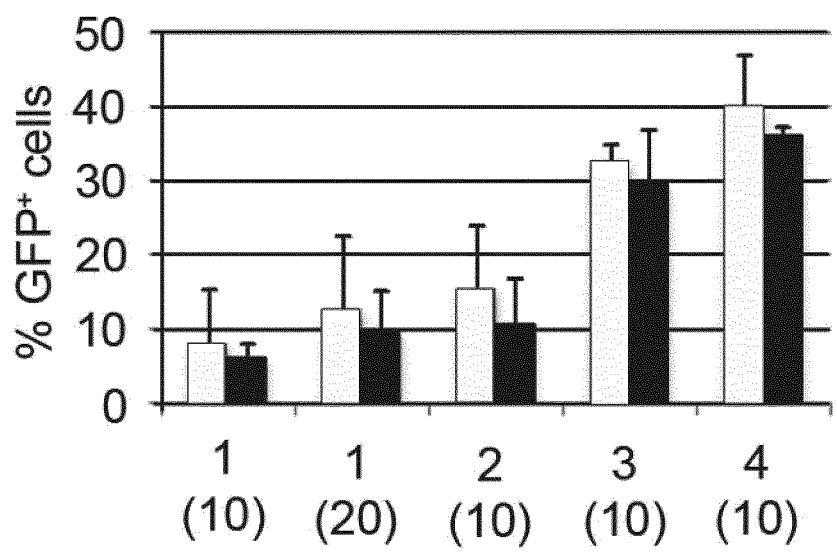

FIG. 15 shows histograms representing the percentage of IL-7 prestimulated memory T cells (white bars) and naïve T cells (black bars) expressing GFP after transduction by VSV-G (1), RD114/TR (2), BaEV/TR (3) or BaEVRLess (4) pseudotyped lentiviral vector particles at MOIs indicated into brackets.

Figure 16:
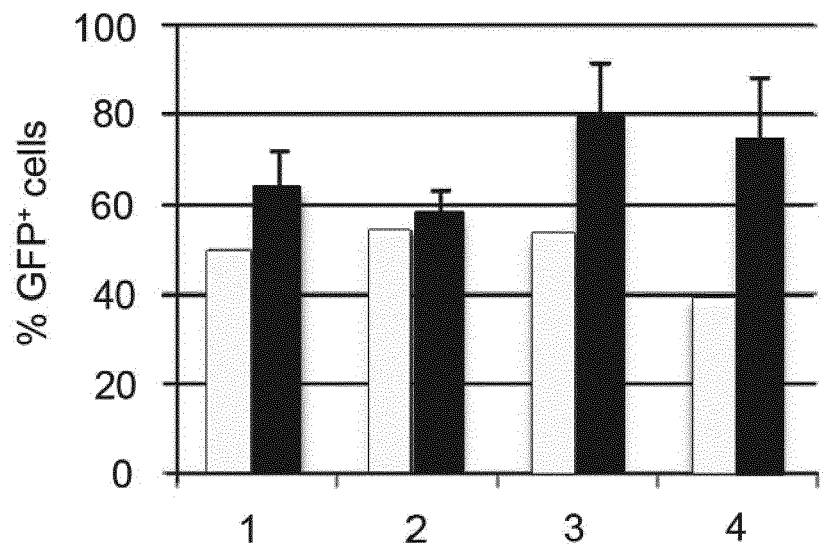

FIG. 16 shows histograms representing the percentage of TCR prestimulated T cells expressing GFP after transduction, in presence of retronectin (black bars) or not (white bars), by VSV-G (1), RD114/TR (2), BaEV/TR (3) or BaEVRLess (4) pseudotyped lentiviral vector particles at MOIs of 10.

Figure 17:
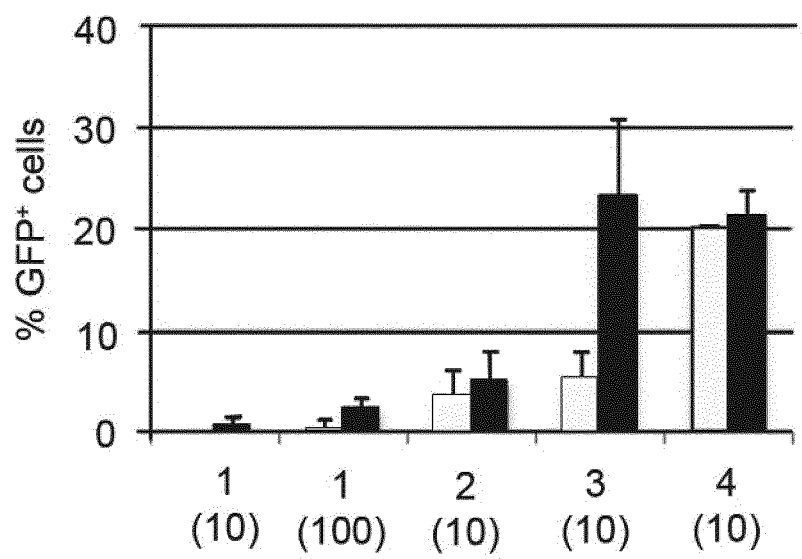

FIG. 17 shows histograms representing the percentage of resting B cells expressing GFP after transduction, in presence of retronectin (black bars) or not (white bars), by VSV-G (1), RD114/TR (2), BaEV/TR (3) or BaEVRLess (4) pseudotyped lentiviral vector particles at MOIs indicated into brackets.

Figure 18:
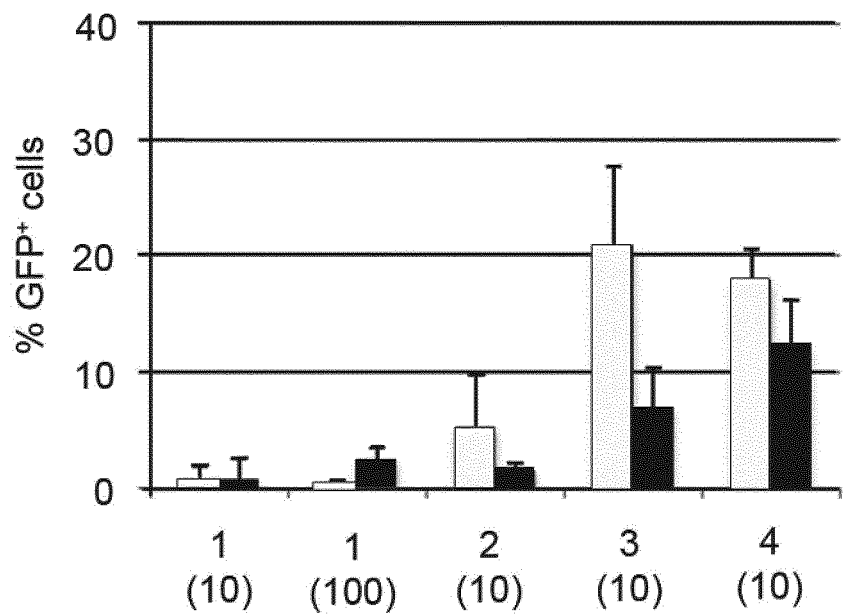

FIG. 18 shows histograms representing the percentage of memory resting B cells (white bars) and naïve resting B cells (black bars) expressing GFP after transduction by VSV-G (1), RD114/TR (2), BaEV/TR (3) or BaEVRLess (4) pseudotyped lentiviral vector particles at MOIs indicated into brackets.

Figure 19:
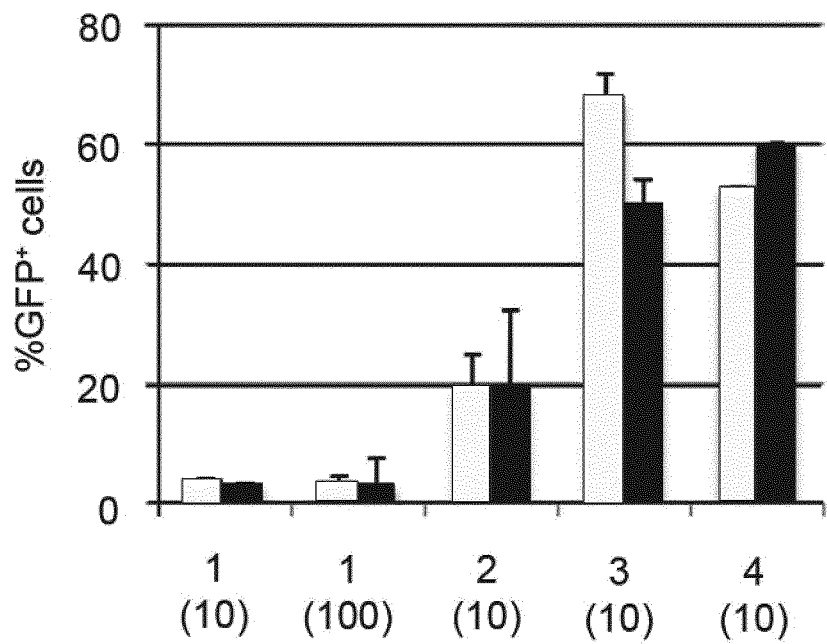

FIG. 19 shows histograms representing the percentage of BCR prestimulated memory resting B cells (white bars) and naïve resting B cells (black bars) expressing GFP after transduction by VSV-G (1), RD114/TR (2), BaEV/TR (3) or BaEVRLess (4) pseudotyped lentiviral vector particles at MOIs indicated into brackets.

Figure 20:
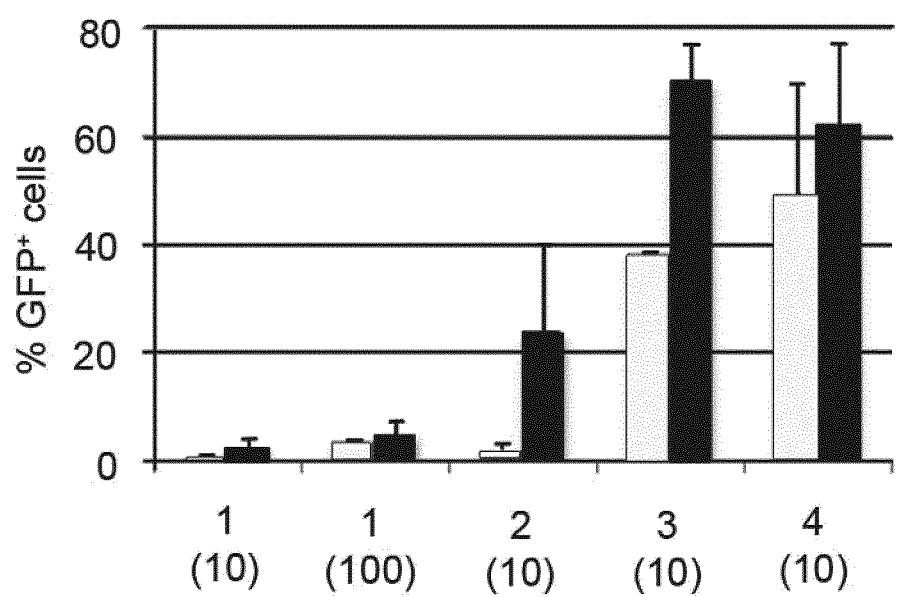

FIG. 20 shows histograms representing the percentage of MZL B cells expressing GFP after transduction, in presence of retronectin (black bars) or not (white bars), by VSV-G (1), RD114/TR (2), BaEV/TR (3) or BaEVRLess (4) pseudotyped lentiviral vector particles at MOIs indicated into brackets.

Figure 21:
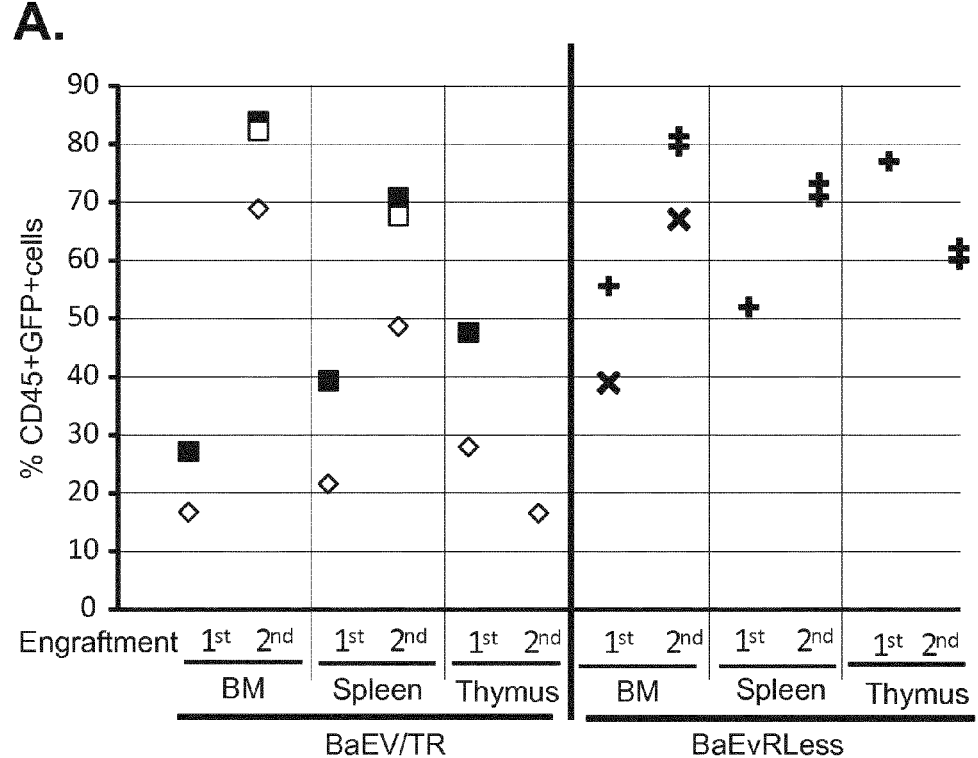
Figure 21:
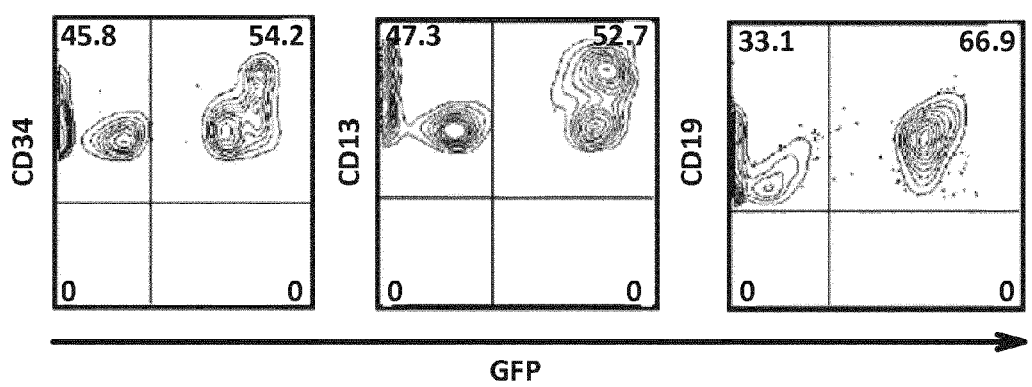

FIG. 21A shows graphs representing the percentage of GFP+ hCD45+ cells detected by FACS after $1^{st}$ and $2^{nd}$ engraftments of mice. Cord blood hCD34+ cells were pre-stimulated with a cytokine cocktail (TPO+SCF+Flk-3L) for 16 h and transduced with BaEV/TR-LVs and BaEVRLess-LVs at an MOI=10 for 36 h. Subsequently the cells ($2\times10^5$) were injected into the liver of irradiated newborn NOD/SCID γc−/− mice (NSG mice). Upon reconstitution for 8-9 weeks, the different hematopoietic tissues (bone marrow, spleen and thymus) of these primary mice engraftments ($1^{st}$) were analysed for human cell engraftment by anti-hCD45 staining. The percentage of GFP+ hCD45+ cells detected by FACS is indicated for each vector type and each hematopoietic tissue. Subsequently, the hCD34+ cells were isolated from the bone marrow of each of these primary engrafted mice, and $1-2\times10^5$ isolated hCD34+ cells were injected in one or two mice following the same procedure as for the primary engraftments. 8-9 weeks upon engraftment, these secondary ($2^{nd}$) engrafted mice were analysed for transduced human cell engraftment (hCD45+ GFP+) in the bone marrow, spleen and thymus. The primary and corresponding secondary engraftments are indicated by the same symbol. FIG. 21B shows graphs representing the detection of GFP+ human B-cells (CD19+), human immature progenitor cells (CD34+) and myeloid progenitor cells (CD13+) by FACS in a bone marrow sample of a representative secondary recipient NSG mice for BaEV/TR-LV transduction.

Figure 22:
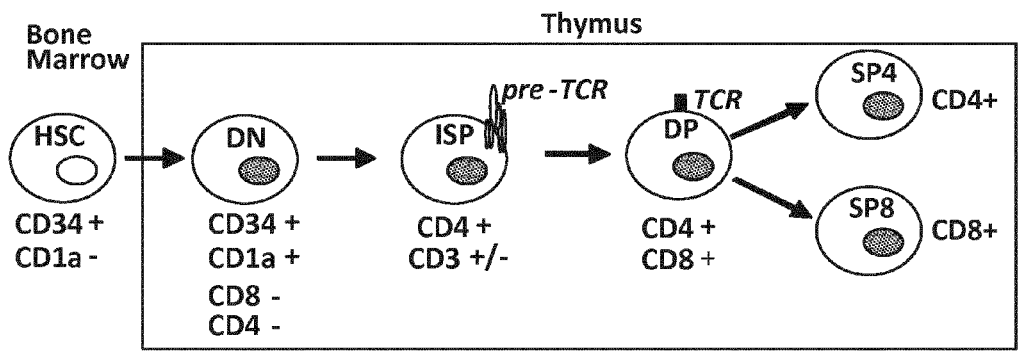
Figure 22:
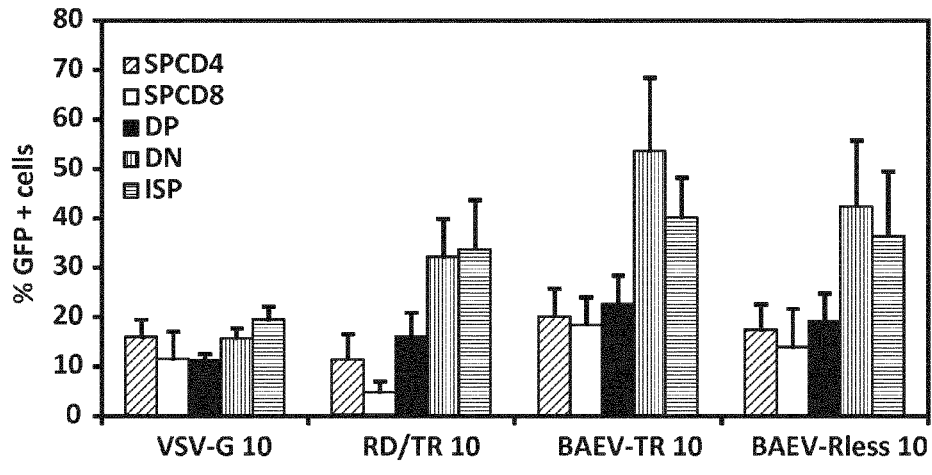
Figure 22:
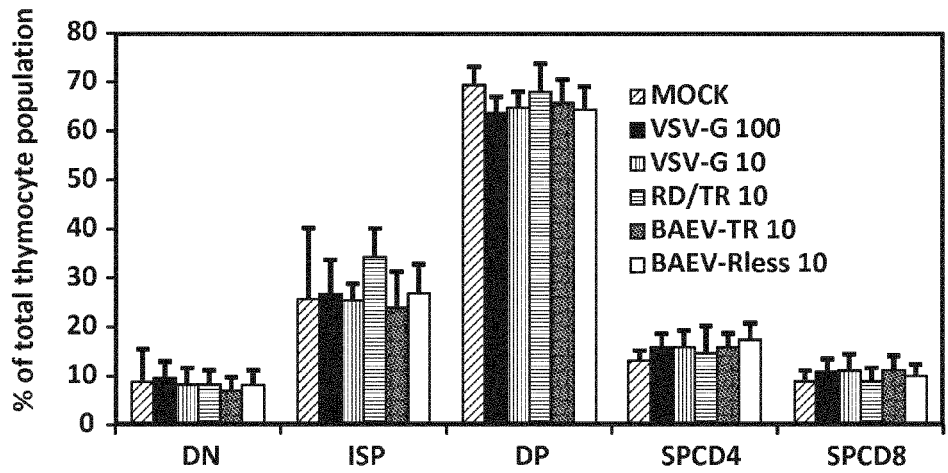

FIG. 22A shows the schematic presentation of thymocyte differentiation. HSC, hematopoietic stem cell; DN, double negative; ISP, immature CD4 single positive cells; DP, double positive; SP4, single positive CD4+; SP8, single positive CD8+; TCR, T cell receptor. FIG. 22B shows histograms representing the percentage of freshly isolated thymocytes expressing GFP after transduction in the presence of IL-7 (20 ng/ml) with VSV-G-, RD114/TR-, BaEV/TR-, and BaEVR-Less-LVs encoding the GFP reporter at an MOI of 10. Upon multiple staining for CD3, CD4 and CD8 the transduction in the different thymocyte subpopulations were determined by FACS. FIG. 22C shows histograms representing the distribution of the different thymocyte subpopulations upon incubation of the total thymocytes with the different vectors as compared to untransduced thymocytes.

Figure 23:
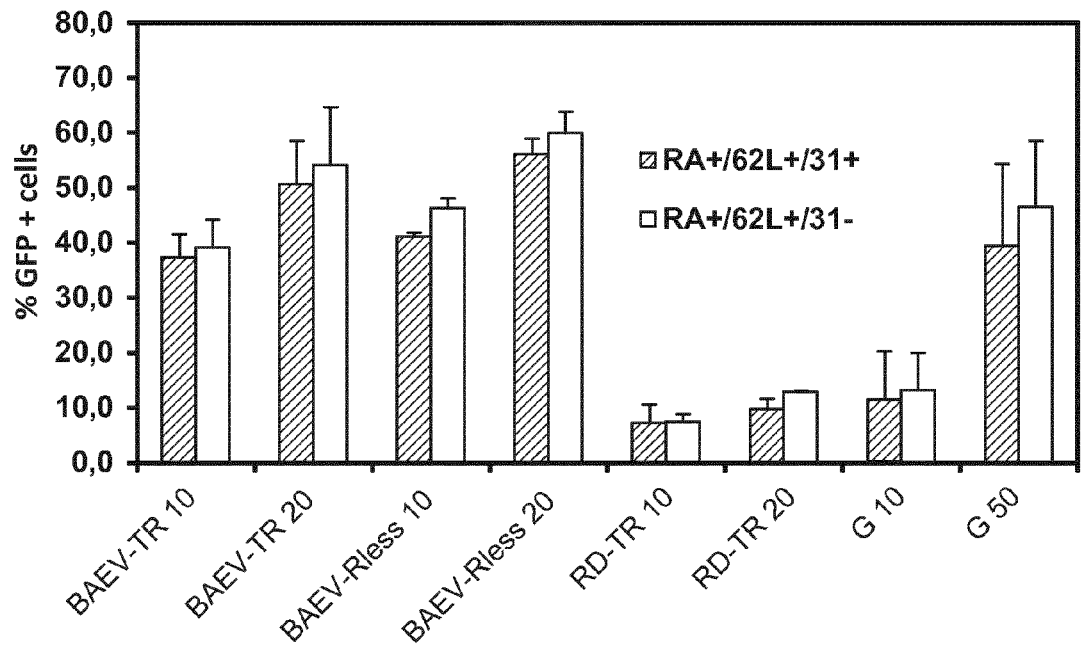
Figure 23:
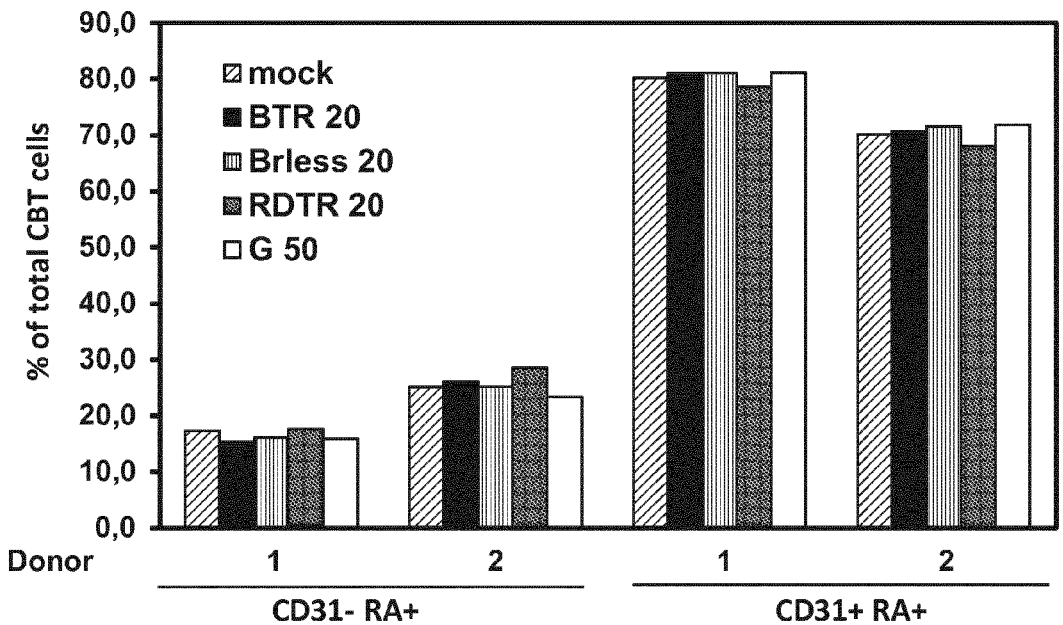

FIG. 23A shows histograms representing the percentage of freshly isolated total CB T cells expressing GFP after pre-stimulation with IL-7 for 48 h and subsequent transduction with the different vectors: VSV-G-, RD114/TR-, BaEV/TR-, and BaEVRLess-LVs encoding the GFP reporter at an MOI of 10 or 20, or VSV-G-LVs at an MOI of 50. At day 3 of transduction cells were stained for human surface marker: CD45RA, CD62L, CD31 and the transduction efficiencies in the recent thymocyte emigrants (RA+/62L+/31+) and more mature naive CB T cells (RA+/62L+/31−) were determined by FACS analysis. FIG. 23B shows histograms representing the distribution of the different naïve CB T cell subpopulations upon incubation of CB T cells with the different vectors as compared to untransduced T cells.

EXAMPLE

The following example demonstrates the advantageous properties of BaEV/TR- and BaEVRLess pseudotyped lentiviral vector particles for use as gene transfer vehicle as compared to previous pseudotyped lentiviral vectors.

Materials and Methods
Production of Lentiviral Vectors and Titering

Self-inactivating HIV-1-derived vectors were generated by transient transfection of HEK 293T cells, a human embryo kidney cell line (American Type Culture Collection, Rockville, Md., CRL-1573). $2.6\ 10^6$ HEK 293T cells were seeded onto 10-cm$^2$ tissue culture dishes 24 h before transfection. 293T cells were grown in Dulbecco modified Eagle medium (DMEM, Invitrogen) supplemented with 10% fetal calf serum (FCS). Cells were transfected by Ca-phosphate precipitation with 8.6 μg of the Gag-Pol packaging construct 8.91 and the GFP-encoding HIV-1 derived SIN transfer vector pHIV-SFFV-GFP-SIN and either 2.5 μg of pMD.G, encoding the VSV-G glycoprotein (GP), or 7 μg of phCMV-RD114/TR, phCMV-BaEVWT, phCMV-BaEV/TR or phCMV-BaEVRLess. At 16 h post-transfection, the DMEM medium was replaced by serum-free medium (Opti-MEM, Invitrogen) and 36 h after transfection, vectors were harvested, filtrated through 0.45 μm pore-sized membrane and concentrated using an ultra-filtration concentration system (Vivaspin, Satorius; 2 h at 3000 g (4° C.)) or by low-speed concentration by centrifugation of the viral supernatant at 3000 g at 4° C. overnight or by ultracentrifugation (4° C., 25000 rpm, 2 h). Subsequently, vectors were stored at −80° C. To determine transduction efficiency and infectious titers of HIV vectors, serial dilutions of vector preparations were added to 293T cells and percentage of GFP$^+$ cells was determined by flow cytometry 3 days after transduction. The infectious titers are expressed as infectious vector particles per milliliter (Infectious unit IU/mL). Multiplicities of infection (MOIs) were determined on proliferating 293T cells and are indicated in all transduction experiments.

Stability of Pseudotyped Vectors in Human or Macaque Serum.

Infectious pseudotyped HIV or SIV-vector particles (150000 GFP infectious units in 50 μl suspension buffer) were mixed with 50 μl heat inactivated or fresh human sera. As a reference, virions were incubated at 37° C. for 1 h and then used to transduce HEK293T target cells. The relative percentage of transduction of human sera-incubated virions to the transduction of the same virions incubated in FCS was calculated.

Sample Collection and Isolation of Human CD34+ Cells

Umbilical cord blood (CB) samples from full-term pregnancies were collected in sterile tubes containing anti-coagulant (SIGMA) after informed consent according to the Helsinki declaration. Low-density PBMC cells were separated by centrifugation over a Lymphoprep cushion (Axis shield). CD34$^+$ stem/progenitor cells were purified from the mononuclear cell fraction with a CD34 magnetic isolation kit (Miltenyi MACS, Miltenyi Biotec) according to the manufacturer's instructions. Purity of the selected CD34$^+$ fraction was assessed by FACS analysis with an APC-conjugated anti-CD34 antibody (BD Pharmingen) and exceeded 95% for all experiments. Subsequently, CD34$^+$ cells were frozen in FCS (Fetal calf serum, Lonza), 10% DMSO and stored at −80° C.

T Cell and B Cell Isolation and Lentiviral Transduction

Adult peripheral blood samples, obtained from healthy adult donors after informed consent, were collected in acid citrate dextrose (ACD) containing tubes. CD3$^+$ T-cells and CD19$^+$ B cells were purified by negative selection using the Rosette tetrameric complex system (StemSep Technologies, Vancouver, Canada). Purity of isolated B- and T-cells was monitored using anti-hCD19APC and anti-hCD3APC antibodies, respectively, and was analyzed by fluorescence-activated cell sorting (FACScalibur; BD). T and B lymphocytes were cultured in RPMI 1640 medium (GibcoBRL Invitrogen, Auckland, New Zealand) supplemented with 10% FCS and penicillin/streptomycin. T cells were prestimulated with anti-CD3+anti-CD28 antibodies (1 µg/ml) in presence of hIL-2 (1 ng/ml) or were pre-stimulated for 3 days with rIL-7 as described in Verhoeyen et al. (2003) *Blood* 101:2167-2174 (10 ng/ml; BDBiosciences, Le Pont de Claix, France). B cells were immediately seeded for transduction or pre-stimulated with *Staphylococcus Aureus* Cowan (SAC; 0.001%; Calbiochem, San Diego, Calif.)+IL-2 (1 ng/ml; SIGMA) as described in Levy et al. (2010) *Blood* 116:498-500. Briefly, 1E5 cells were seeded in 48-well-plates and concentrated vector was added at indicated doses. The percentage of GFP$^+$ cells was determined by FACS 72 h post-transduction. Transduced T-cell cultures were continued in RPMI supplemented with rhIL-7, replenished every 3 days and harvested for FACS analyses, qPCR and Alu-PCR. B-cells were transferred to MS5 cell monolayer in RPMI supplemented with 10% AB serum, 5% FCS, 50 ng/ml rhSCF, 10 ng/ml rhIL-15 and 5 ng/ml rhIL-2 and medium was refreshed every 4 days.

Isolation of Macaque Bone Marrow CD34+-Cells

Adult male cynomolgus macaques (*Macaca fascicularis*) 3-4.5 kg were imported from Mauritius and housed in single cages within level 2 biosafety animal facilities (CEA, Fontenay-aux Roses), in accordance with national guidelines. All experimental procedures were conducted in accordance with European guidelines for animal care. Studies were conducted under protocols approved by the regional committee for animal experimentation. All procedures and blood samplings were performed after animals had been anesthetized with ketamine 10 mg/kg (Imalgène 1000).

Bone marrow mononuclear cells were obtained from the humeri and iliac crest by aspiration and isolated by standard Ficoll density-gradient centrifugation. Cells were washed twice in phosphate buffered saline (PBS) and resuspended in PBS/1% FCS. The fraction was then enriched in CD34$^+$ cells by positive immunomagnetic selection (clone 561; Dynabeads M-450 CD34; Dynal) accordingly to the manufacturer's instructions. Following immunoselection, the CD34$^+$ cell purified fraction was stained using an anti-CD34 monoclonal antibody (clone 563, BD-Pharmingen). Purity of the CD34$^+$ selected cells ranged from 85-95%.

Transduction of Human and Macaque HSCs.

Human and macaque CD34$^+$ cells were incubated overnight in 24-well plates in serum-free medium (CellGro, CellGenix) supplemented with antibiotics (PENSTREP, Invitrogen) and with human recombinant cytokines (as indicated): stem cell factor (rSCF, 100 ng/ml), Thrombopoietin (TPO, 20 ng/ml) and Flt3 ligand (Flt3-L, 100 ng/ml) (Preprotech) for human CB CD34$^+$ cells. For cynomolgus macaque bone marrow CD34$^+$ cells, human recombinant interleukin (IL-6) (20 ng/ml) and interleukin (IL-3) (20 ng/ml) (Preprotech) were added to the previous cocktail. $5 \cdot 10^4$ prestimulated CD34$^+$ cells were transduced in 48-well plates with concentrated lentiviral vector supernatant at MOIs of 1, 5, 10, 20 or 100 (as indicated) in serum-free medium (CellGro, CellGenix). Where indicated, transductions were performed on retronectin coated plates (recombinant human fibronectin fragment CH-296) (Takara). On day 3 after transduction, cells were replenished with cytokines. After 3 and 6 days of transduction, percentage of GFP$^+$ cells was determined by flow cytometry.

Clonogenic Assay of CD34$^+$ Cells

CD34$^+$ cells were transduced as described herein above, washed in PBS (Invitrogen) and plated at a density of 1000 cells/ml in complete methylcellulose medium (1% methylcellulose, 15% FBS, 1% BSA, bovine pancreatic insulin [1 µg/ml], iron-saturated transferrin [200 mg/ml], 10-4 M 2-mercaptoethanol, 2 mM L-glutamine, SCF [50 ng/ml], IL-3 [10 ng/ml], IL-6 [10 ng/ml], erythropoietin [3 U/ml]) (Stem Cell technologies). GFP$^+$ colonies were scored by light and fluorescence microscopy 14 days after seeding.

Western Blot Analysis

BaEVwt, BaEV/TR and BaEVRLess pseudotyped LVs were purified over a sucrose-cushion by ultracentrifugation (2 h, 25000 rpm, 4° C.) and were frozen after resuspension in PBS. The upper part of the membrane was stained with antibodies against the surface domain of BaEV glycoprotein, the lower part of the membrane was stained with antibodies against the p24 HIV-1 capsid to assess equivalent loading of purified vectors. The positions of the BaEV mutant glycoproteins and the HIV capsid were indicated.

Animals

BALB/c Rag2$^{-/-}$, γc$^{-/-}$ immunodeficient mice were obtained from Dr Mamoro Ito, and Taconic (CIEA, Kawasaki, Japan). All mice used were housed in the animal facility of the Ecole Normale Superieure de Lyon, France (PBES). The animals were kept the whole time of the experiment under sterile conditions and all experiments were performed in accordance with the guidelines of the Institutional animals care upon approval of protocols by the local ethical committee.

Conditioning and Reconstitution of Balb-c Rag2$^{-/-}$, γc$^{-/-}$ Mice

The 2- to 4-day-old newborn BALB/c Rag2$^{-/-}$, γc$^{-/-}$ mice were subjected to a sublethal irradiation of 2×1.5Gy. For evaluation of reconstitution/differentiation capacity of transduced hCB-CD34$^+$ cells, the latter cells were transduced at an MOI of 10 with BaEV/TR-, BaEVRLess-, RD114/TR-, VSV-G-LVs and 48 h after transduction, $2.10^5$ cells were injected intra-hepatically into newborn mice. At 10-12 weeks of human cell engraftment, peripheral blood was taken from the facial vein to check the reconstitution efficiency by analyzing the percentage of human engraftment (hCD45$^+$ cells) by FACS.

FACS Analysis

The mice were sacrificed at 10-12 weeks of human cell engraftment in agreement with bioethical procedures and all hematopoietic tissues were harvested. Subsequently the cells from bone marrow, spleen, thymus and peripheral blood were extracted. For the detection of LV transduction of the engrafted cells, flow cytometry analysis was performed using APC-coupled anti-hCD45 antibody for the detection of total human cell engraftment in the bone marrow. APC-coupled antibodies (BD Pharmingen) were used for the detection of hCD19 (B cells), hCD34 (early progenitor cells) and hCD13 (myeloid progenitors).

Results

Figure 1:
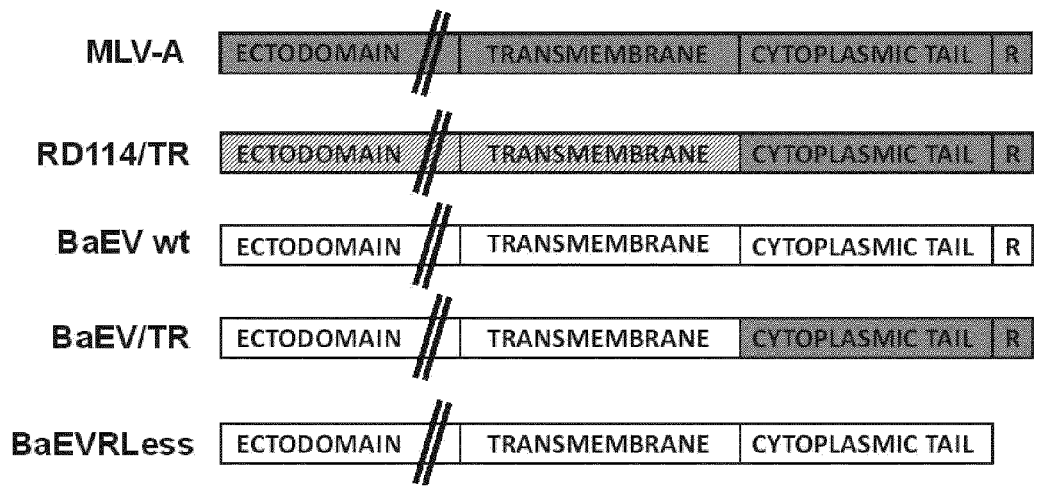
FIG. 1 shows schematic representation of the BaEV wild-type glycoprotein, the RD114/TR and BaEV/TR chimeric glycoproteins and the BaEVRLess glycoprotein. The cytoplasmic domain of RD114 and BaEV wild-type glycoprotein was exchanged for the one of the MLV-A glycoprotein resulting in the chimeric RD114/TR and BaEV/TR glycoproteins respectively. The R peptide of the cytoplasmic tail of BaEV wild-type glycoprotein was deleted resulting in a BaEVRLess mutant glycoprotein.

The Mutant BaEV/TR Glycoprotein and BaEVRLess Glycoprotein can Pseudotype HIV-1 Vector Efficiently The BaEV/TR chimeric glycoprotein was engineered by the inventors by exchange of its cytoplasmic domain for the one of the MLV-A glycoprotein (FIG. 1). A second mutant was engineered by the deletion of the fusion inhibitory R peptide from the carboxy-terminal cytosolic domain resulting in BaEVRLess glycoprotein (FIG. 1). The inventors compared these different mutant BaEV glycoproteins in their ability to pseudotype lentiviral vectors derived from HIV-1 to VSV-G and RD114/TR glycoproteins.

RD114/TR, BaEV/TR, BaEVRLess and VSV-G pseudotyped HIV vectors were generated by transient transfection in HEK293T cells together with the gagpol packaging and HIV vector encoding for GFP. The vector supernatants were concentrated by low speed or ultracentrifugation (100-fold).

Figure 2:
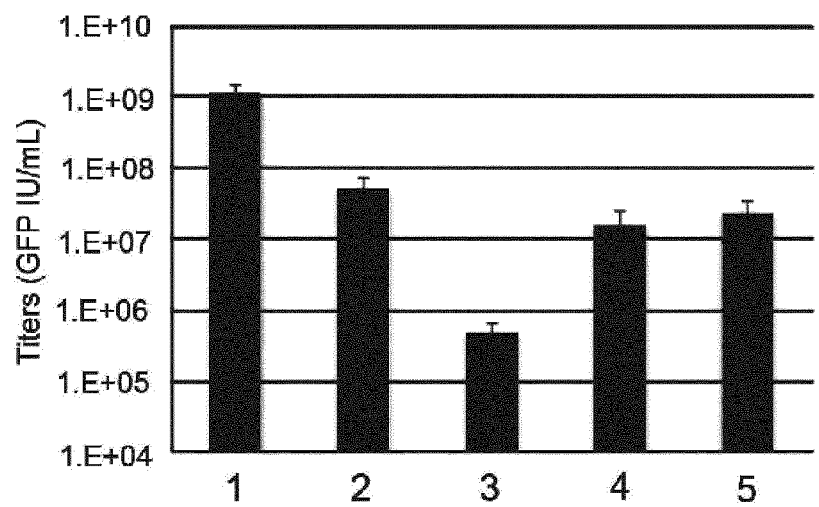
FIG. 2 shows histograms representing the titers of the different pseudotyped lentiviral vector particles (VSV-G (1), RD114/TR (2), BaEVwt (3), BaEV/TR (4) and BaEVRLess (5) pseudotyped) coding for the GFP marker gene obtained by infection of HEK293T cells with serial dilutions of concentrated vector preparations. The percentage of GFP$^+$ cells was determined by cytometry 3 days after infection. Infectious titers were calculated as GFP infectious units (IU)/ml. Averages are showed (n=7) except for BaEVwt (n=3).

Infections assays on HEK293T cells indicated that titers higher than $1 \cdot 10^7$ IU/ml were obtained for BaEV/TR and BaEVRLess pseudotyped LVs resulting in a 40-fold titer increase as compared to BaEVwt-LVs. RD114/TR and VSV-G pseudotyped vectors gave titers of $6 \cdot 10^7$ IU/ml and $1 \cdot 10^9$ IU/ml (FIG. 2). The immunoblot confirmed a lower incorporation of the BaEVwt glycoprotein on the lentiviral vector surface as compared to BaEV/TR and BaEVRLess glycoproteins at equal amount of HIV-1 capsid. These data were in agreement with the increase in titers obtained for BaEV/TR and BaEVRLess pseudotyped LVs as compared to BaEVwt-LVs.

Infectious titers of BaEV mutant glycoproteins pseudotyped LVs (BaEV/TR and BaEVRLess) were similar to the ones of RD114/TR-LVs and were therefore further considered for transduction of human CD34$^+$ early progenitor cells and T and B cells.

Figure 3:
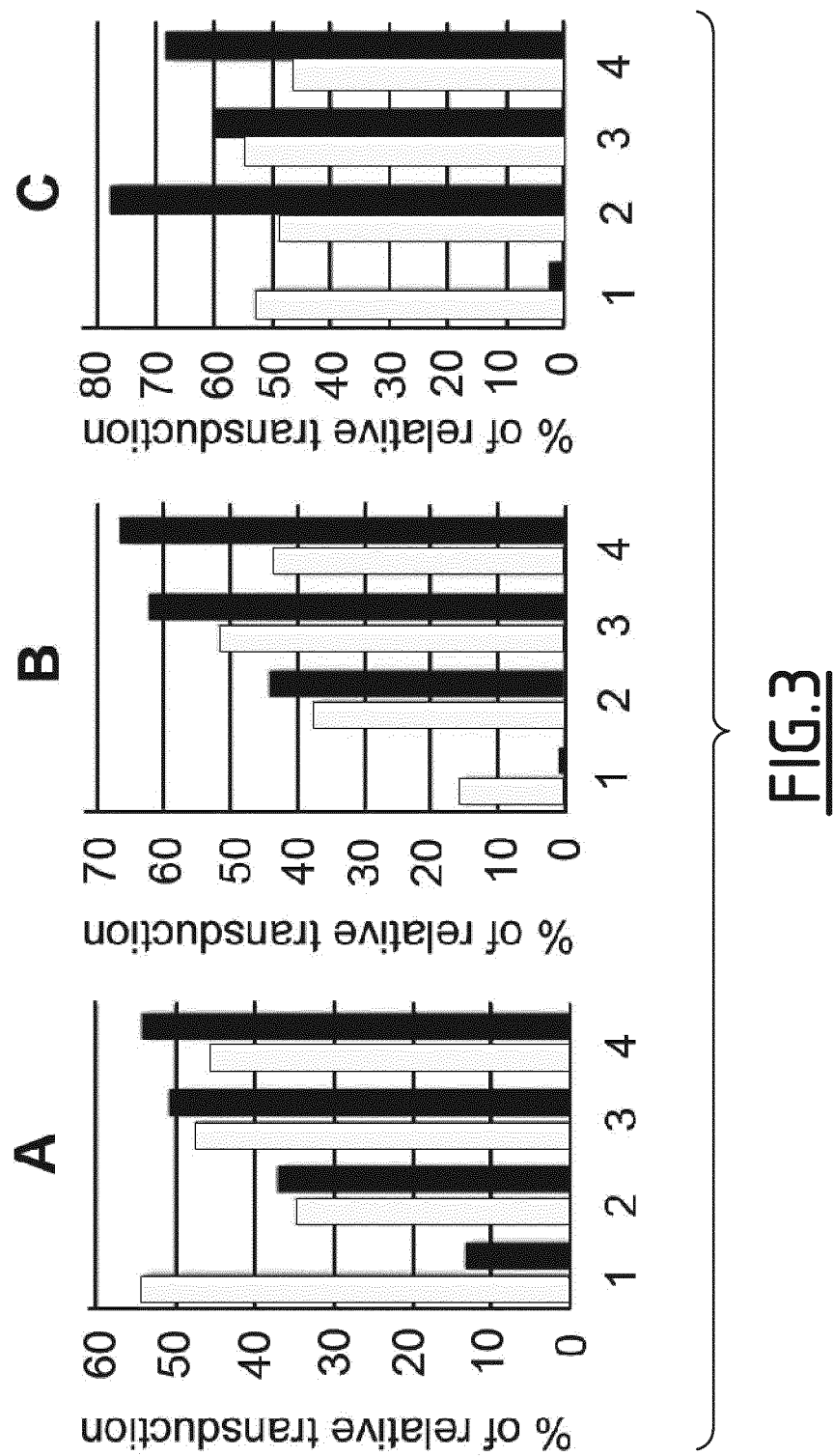
FIG. 3 shows histograms representing the relative percentage of transduction of HEK293T cells by VSV-G (1), RD114/TR (2), BaEV/TR (3) or BaEVRLess (4) pseudotyped lentiviral vector particles which were incubated at 37° C. for 1 hour in heat inactivated human sera (white bars; the serum was heat-inactivated at 56° C. before incubation with the vectors to inactivate the complement where fresh serum contains active complement) or in fresh human sera (black bars) relative to the transduction of the same virions incubated in FCS. The values of vector incubations with sera of 3 different donors (A, B and C) are shown.

Stability of BaEV Mutant Pseudotyped Vectors and Resistance to Human Serum Inactivation In view of clinical in vivo application, BaEV mutant pseudotyped LVs must resist to the human complement system. This stability was determined by comparing infectious titers of LVs incubated in human sera 1 hour at 56° C. Heat is reported to destroy human complement, so heat inactivated human sera were used as control. Residual infectious titers obtained were reported to the infectivity of LVs incubated with fetal calf serum (100%) (FIG. 3). As expected the VSV-G pseudotyped LVs were inactivated by the 3 different human sera. BaEV/TR and BaEVRLess pseudotyped LVs remained stable in presence of complement containing sera since no reduction in transduction efficiency was detected upon incubation in the presence of human complement for the three different donors. Thus, the inventors concluded that BaEV/TR and BaEVRLess LVs were resistant to the human complement system to the same extent as RD114/TR-LVs. The stability of BaEV mutant pseudotyped LVs in human serum makes them better candidates than VSV-G LV pseudotypes for in vivo applications.

BaEV Pseudotyped LVs are Highly Superior Over VSV-G- and RD114/TR-LVs for the Transduction of Human CD34$^+$ Cells Both BaEV/TR and BaEVRLess pseudotyped LVs bind to hASCT1 and hASCT2 on the cell membrane of hCD34$^+$ cells while the RD114/TR LVs only bind to hASCT2. It was described previously that RD114/TR-LVs can only transduce hCD34$^+$ cells efficiently in the presence of retronectin. Indeed, retronectin is a fragment of fibronectin that is reported to allow binding of both cells and vectors and therefore increases transduction of hCD34$^+$ cells. To evaluate the role of retronectin in BaEV pseudotyped LVs transduction, the inventors initially prestimulated hCD34$^+$ cells with a strong cytokine cocktail (rSCF+rTPO+rFlt3-L) and transduced them with VSV-G, RD114/TR, BaEV/TR, BaEVRLess pseudotyped LVs at a MOI of 10 in wells coated or not with retronectin. The inventors observed that, in the presence of retronectin, both BaEV-LVs transduced hCD34$^+$ cells at more than 70%.

As mentioned above, a strong stimulation with a cytokine cocktail will induce HSCs into differentiation and their loss of self renewal capacity. Indeed, the less the cells are prestimulated, the less they differentiate and the more they keep their 'stem cell' character. Moreover, the stronger the cytokine stimulation the higher the risk is that multiple vector integrations per cell will occur at high vector doses. This might increase the risk of genotoxicity in gene therapy applications. Therefore, the inventors tested if BaEV pseudotyped LVs could transduce efficiently hCD34$^+$ cells after a low cytokine prestimulation combined with low vector doses.

Figure 4:
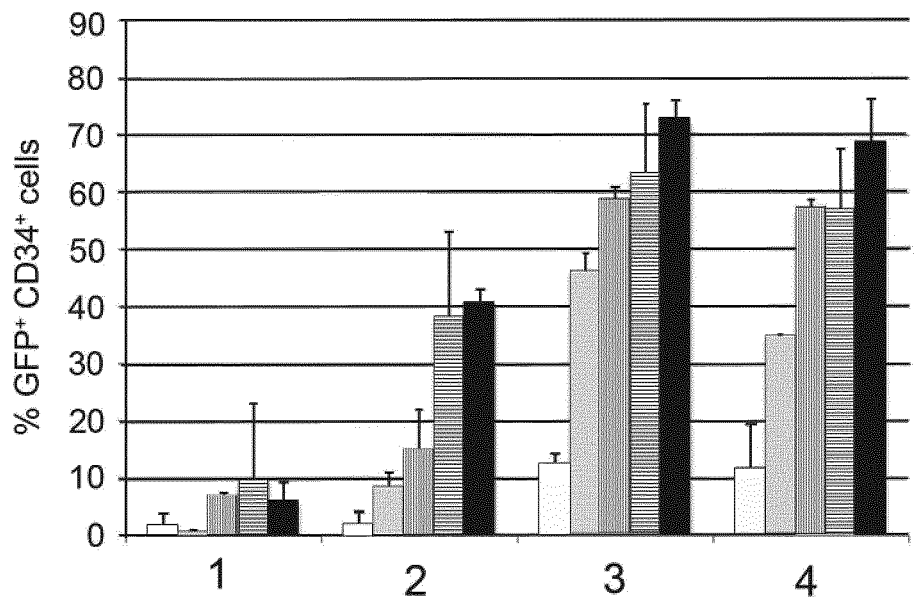
FIG. 4 shows histograms representing the percentage of transduction of unstimulated (white bars), SCF prestimulated (dashed bars), TPO prestimulated (vertical hatched bars), SCF+TPO prestimulated (horizontal hatched bars) or SCF+TPO+Flt3-L prestimulated (black bars) human CD34$^+$ cells by VSV-G (1), RD114/TR (2), BaEV/TR (3) or BaEVRLess (4) pseudotyped lentiviral vector particles at MOI of 10. Analysis for GFP expressing cells was performed 6 days after transduction.

Firstly, they applied vectors at a fixed MOI (number of infectious particles per cells) of 10 and different cytokine prestimulation protocols for hCD34$^+$ cells (FIG. 4): 1) no stimulation; 2) stimulation with a single cytokine: rSCF or rTPO; 3) rSCF and rTPO; 4) rSCF+rTPO+rFlt3-L Importantly, the strongest cytokine pre-stimulation used here was lower than stimulation cocktails currently used in clinical setting with the objective to limit cell differentiation. The inventors observed that a single TPO stimulation was sufficient for a transduction of hCD34$^+$ cells up to 60% for BaEV pseudotyped LVs, while VSV-G-LVs and RD114/TR-LVs transduced only 8-20% hCD34$^+$ cells upon TPO stimulation. SCF single prestimulation permitted up to 30-50% hCD34$^+$ cell transduction while VSV-G-LVs and RD114/TR-LVs did only reach transduction levels of 10%. A combination of TPO+SCF or TPO+SCF+FLK-3 prestimulation with a single BaEV-LV incubation resulted in up to 75% hCD34$^+$ cell transduction, while RD114/TR-LVs achieved not more than 40% of transduction. Concluding, for all the different cytokine prestimulation protocols BaEV LV pseudotypes outperformed VSV-G- and RD114/TR-LVs for hCD34$^+$ cell transduction. Moreover, results obtained on unstimulated cells indicated that BaEV/TR LVs and BaEVRLess LVs were able to transduce 10-20% of unstimulated hCD34$^+$ cells in the presence of retronectin. In contrast, VSV-G- and RD114/TR LVs were unable to transduce unstimulated quiescent hCD34$^+$ cells efficiently at the same vector doses (MOI=10).

Figure 5:
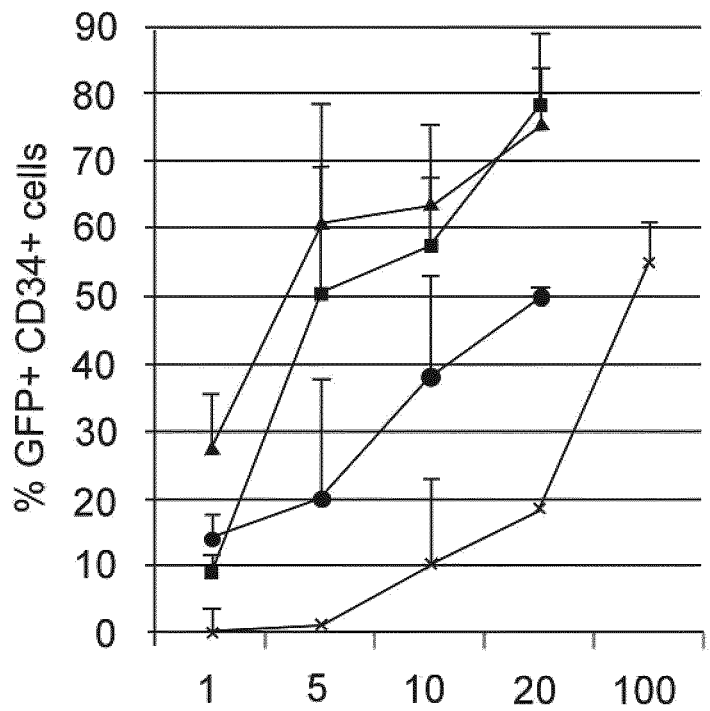
FIG. 5 shows graphs representing the percentage of transduction of SCF/TPO prestimulated CD34$^+$ cells by VSV-G (×), RD114/TR (●), BaEV/TR (▲) or BaEVRLess (■) pseudotyped lentiviral vector particles at MOIs of 1, 5, 10, 20

Secondly, the risk of insertional mutagenesis must be avoided to limit gene therapy side effects. Therefore, the inventors decreased the vector dose in order to limit multicopy integrations. Different MOIs were tested under rSCF+rTPO and rSCF+rTPO+rFlt3-L stimulations (FIGS. 5 and 6). BaEV/TR pseudotyped LVs transduced notably better hCD34$^+$ cells at low vector doses reaching 60% (rSCF+rTPO) and 70% (rSCF+rTPO+rFlt3-L) at a MOI of 5. BaEVRLess-LVs were highly superior over the RD114/TR-LVs at a MOI of 5. VSV-G LVs, remained at low vector doses (MOI 5-10) much less efficient. Only at an MOI of 100 these VSV-G-LVs allowed efficient transduction of hCD34$^+$ cells, a vector dose currently used for clinical gene therapy trials. But the VSV-G-LV transduction rate remained far below that of BaEV-LV (VSV-G-LVs (MOI of 100)=50-60% and BaEV-LVs (MOI 20)=75-90%; FIGS. 5 and 6). Under the higher stimulation condition, the inventors noted that BaEV/TR-, BaEVRLess-LVs and RD114/TR-LVs reached a plateau at a MOI of 10 for BaEV/TR-LVs and RD114/TR LVs (75% and 50% of transduction respectively). Consequently, incubation with low vector doses of BaEV LVs inferior or equal to 10 were sufficient to transduce hCD34$^+$ cells very efficiently and to a much higher extent than RD114/TR-LVs and VSV-G LVs. In conclusion, BaEV pseudotyped LVs and particularly BaEV/TR-LV appeared to be more effective to transduce hCD34$^+$ cells than the currently available VSV-G-LV and RD114/TR-LV vectors. Clearly, the VSV-G-LV hCD34$^+$ cell transduction efficiency is dependent on the cytokines stimulation cocktail while for the BaEV pseudotyped LVs this is not the case.

Low BaEV-L V Vector Doses Allow Transducing at a High Rate Short Term Progenitors.

The inventors wanted to confirm that the high hCD34$^+$ cell transduction obtained with BaEV pseudotypes were due to stable transduction of short term progenitors. Thus, they determined the transduction efficiency of BaEV pseudotyped LVs on hematopoietic progenitors thanks to a clonogenic assay performed in a semi-solid methylcellulose medium.

Cells prestimulated with rSCF+rTPO and rSCF+rTPO+ rFlt3-L were transduced with RD114/TR, BaEV/TR, BaEVRLess pseudotyped vectors at a MOI of 10 and VSV-G at a MOI of 100. The inventors chose a higher MOI for VSV-G because clinical trials currently work with a MOI of 100 for this pseudotype to transduce hCD34$^+$ cells. It thus appeared more relevant to use this high vector dose for comparison. Three days after transduction, cells were cultured in a methylcellulose medium (complemented with cytokines) which allowed their differentiation into myeloid colonies. The inventors observed after 14 days erythroblastic, granulomonocytic and mixed colonies expressing GFP or not. First, they compared the number of GFP expressing colonies for different prestimulations (FIG. 7). For all vectors tested, both stimulations gave similar results. The proportion of clonogenic progenitors transduced with both BaEV mutant pseudotyped vectors at a MOI of 10 was higher than with VSV-G ones at a MOI of 100 (BaEV/TR-LV=50-70%, BaEVRLess-LV=45-70%, VSV-G-LV=25-50%). At the same vector dose used for BaEV/TR and BaEVRLess pseudotyped LVs, only 10-35% of clonogenic progenitors were transduced with RD114/TR LV pseudotypes. There was no significant difference between the proportion of RD114/TR-, BaEV/TR-, BaEVRLess LV transduced CD34$^+$ cells after a rSCF+ rTPO prestimulation and the clonogenic progenitors derived from them indicating that hCD34$^+$ cell transduction was stable (FIG. 8). In contrast, for VSV-G LVs, the proportion of transduced clonogenic progenitors was significantly lower than the rate of transduced CD34$^+$ cells they were derived from (FIG. 8) suggesting that VSV-G pseudotyped vectors transduced more differentiated CD34$^+$ cells or were more toxic than other vectors tested.

These results showed that BaEV/TR- and BaEVRLess-LV pseudotypes stably transduced at a high rate short term repopulating progenitor cells.

BaEV Pseudotyped LVs Transduce at High Efficiency Repopulating Hematopoietic Progenitors in Immunodeficient Mice To determine the transduction efficiency of both BaEV mutant pseudotyped vectors on repopulating hematopoietic progenitors, cord blood CD34$^+$ cells were prestimulated 16 h with rSCF, rTPO and FLk-3L and then transduced with RD114/TR, BaEV/TR, BaEVRLess pseudotyped vectors at a MOI of 10 or with VSV-G-pseudotyped LVs at a MOI of 100 and transplanted into sublethally irradiated immunodeficient Balbc, Rag2$^{-/-}$, γc$^{-/-}$ new born mice or NOD/SCID/γc–/– (NSG) mice (Table 1). Both mice models allow engraftment of a complete human blood system since they lack T, B and NK cells.

After 8-10 weeks, the animals were sacrificed and the percentage of total human blood nucleated cells (CD45$^+$) in the bone marrow was determined by FACS analysis (Table 1).

TABLE 1

BaEV/TR- and BaEVRLess-LVs allow efficient transduction of SCID repopulating cells

| Pseudotype | Bone marrow Engraftment (%) | Bone marrow | | | | | Spleen | Thymus |
| --- | --- | --- | --- | --- | --- | --- | --- | --- |
| | | CD45+ GFP+ (%) | CD34+ GFP+ (%) | CD19+ GFP+ (%) | CD13+ GFP+ (%) | CD14+ GFP+ (%) | CD45+ GFP+ (%) | CD45+ GFP+ (%) |
| VSV-G | | | | | | | | |
| 1(*) | 22.1 | 32.0 | 18.3 | 41.0 | 5.7 | 7.7 | NA | NA |
| 2(*) | 2.2 | 6.8 | 27.7 | 15.5 | 9.6 | 4.0 | NA | NA |
| 3(*) | 57.3 | 5.7 | 17.7 | 12.5 | 22.3 | 19.2 | NA | NA |
| RD114/TR | | | | | | | | |
| 1(*) | 32 | 3.2 | 2.9 | 2.8 | 4 | 7 | NA | NA |
| 2(*) | 15.3 | 39.0 | 33.8 | 38.6 | 34.2 | 35.0 | NA | NA |
| 3(*) | 2.3 | 17.6 | 16.5 | 21.8 | 11.3 | 13.5 | NA | NA |
| 4(*) | 34.0 | 27.2 | 40.1 | 27.1 | 24.1 | 18.7 | NA | NA |
| 5(°) | 30.6 | 76.5 | 64.5 | 78.8 | 57.4 | 45.2 | 37.0 | 41.2 |
| 6(°) | 25.3 | 12.6 | 13.8 | 10.0 | 11.1 | 4.8 | 20.5 | 15.8 |
| BaEV/TR | | | | | | | | |
| 1(*) | 23.6 | 36.0 | 41.4 | 39.1 | 37.4 | 56.6 | NA | NA |
| 2(*) | 21.6 | 69.7 | 78.9 | 68.0 | 73.7 | 68.7 | NA | NA |
| 3(°) | 27.6 | 92.0 | 91.7 | 89.7 | 82.5 | 72.7 | 84.2 | 84.3 |
| 4(°) | 36.4 | 59.3 | 40.0 | 59.8 | 68.0 | 33.3 | 69.4 | 65.5 |
| BaEVRLess | | | | | | | | |
| 1(*) | 23.8 | 33.9 | 35.7 | 38.7 | 35.6 | 38.6 | NA | NA |
| 2(*) | 10.0 | 56.2 | 70.2 | 66.1 | 59.3 | 65.5 | NA | NA |
| 4(*) | 17.6 | 70.5 | 64.4 | 76.2 | 67.9 | 67.6 | NA | NA |
| 5(°) | 64.1 | 55.5 | 51.5 | 56.0 | 56.9 | 59.4 | 52.0 | 76.9 |
| 6(°) | 52.8 | 52.8 | 56.0 | 46.6 | 61.1 | 60.0 | 42.5 | 4.1 |
| 7(°) | 89.5 | 87.5 | 83.8 | 86.7 | 83.1 | 83.9 | 69.4 | 74.8 |

(*)Balbc, Rag2–/–, γc–/– mice
(°)NOD/SCID/γc–/– mice

A comparable high level of engraftment with human cells was detected for all transduction conditions (up to 89%, Table 1). However, overall VSV-G-LVs allowed a much lower transduction of scid repopulating cells as compared to the other vectors. For the VSV-G-LVs, the inventors detected 32% transduced hCD45$^+$ cells in the total bone marrow of mice 1 (Table 1). In bone marrow, for VSV-G pseudotyped LV used at a MOI of 100, they observed a transduction bias since a majority of pre-B and pro B cells (CD19$^+$ CD34$^+$ cells) showed 33% of transduction but early progenitors (CD34$^+$ CD19⁻) and myeloid progenitors (CD13⁺) and monocytes (CD14⁺) showed only 5 to 8% of transduction at most (FIG. 9).

In contrast, for BaEV/TR- and BaEVRLess-LVs detailed phenotyping showed that very early progenitor cells (CD34⁺ CD19⁻), as well as B-cell CD19⁺ progenitors and myeloid progenitor CD13⁺-cells were transduced to the same extent since over 30% transduction for all these different cell lineages was detected (FIG. 9). Table 1 shows that BaEV/TR-LVs and BaEVRLess-LVs transduced hCD34⁺ cells resulted in high reconstitution levels in the bone marrow and the highest transduction levels of SCID repopulating cells (up to 90% CD45+GFP+ cells) in the bone marrow. Moreover, these high transduction levels were sustained in the primary recipient mice in all hematopoietic tissues (bone marrow, thymus and spleen Table 1). Equivalent high level transduction was detected for immature progenitors (hCD34+ cells), lymphoid cells (CD19+) and myeloid cells (CD13+ and CD14+) in the bone marrow (Table 1).

For RD114/TR-LVs less than 5% transduction in all the different bone marrow cell lineages was detected for mice NR1. An identical picture was found for progenitors, T and B cells and monocytes in the spleen (FIG. 10). RD114/TR-LVs demonstrated variable transduction levels of SCID repopulating cells (ranging from 3.2-76% of GFP+ CD45+ cells, Table 1).

Overall, these data strongly suggested that BaEV/TR- and BaEVRLess-LVs allowed transduction of very early progenitor repopulating cells, so-called hHSC, able to differentiate into all the different lineages in immunodeficient mice. In contrast, VSV-G LV pseudotypes did not result in equivalent transduction of the different hematopoietic lineages indicating that VSV-G-LVs transduced more differentiated progenitors and less true HSCs as compared to BaEV/TR- and BaEVRLess-LVs.

To confirm that true HSC were gene modified, secondary reconstitutions of NSG mice were performed with bone marrow hCD34 cells of primary NSG mice previously reconstituted with BaEV/TR- and BaEVRLess-LV transduced hCD34+ cells for at least 2 months.
To improve engraftment into secondary recipients the primary NSG bone marrow derived hCD34+ cells were cultured in SCF and TPO to increase or at least maintain the homing capacity of these cells. Following 16-18 h of pre-stimulation, 1-2×10⁵ hCD34+ cells were injected into the liver of newborn NSG mice subjected to sub-lethal irradiation. At 8-9 weeks post-transplantation, the bone marrow, spleen and thymus of the secondary recipient mice were analysed for the percentage of human CD45+ GFP+ cells (FIG. 21A). In the spleen and bone marrow the pourcentage of GFP+ hCD45+ cells was maintained or increased in the secondary recipient mice (FIG. 21A). Moreover, for both BaEV/TR- and BaEVRLess-LVs high levels of GFP+ hCD34+ early progenitor, lymphoid (CD19+) and myeloid (CD13+) cells were detected in the bone marrow of these secondary recipient mice and equivalent percentages of GFP+ cells were detected in these different lineages (FIG. 21B). This indicated that the secondary reconstituting SCID repopulating cells were capable of multilineage differentiation and thus that true human HSC were genetically modified to high levels by BaEV/TR- and BaEVRLess-LVs.

BaEV/TR and BaEVRLess Pseudotyped SIV Vectors Transduce Efficiently Rhesus and Cynomolgus Macaque CD34⁺ Bone Marrow Cells.

Lentiviral vectors based on HIV transduce hCD34⁺-cells very efficiently, while they transduce the corresponding cells from old world monkeys (baboons, rhesus and cynomolgus macaques) very poorly. This is attributed to restriction factors (TRIM5a) interfering at several post-entry steps of HIV in simian cells. Thus, since the cynomolgus macaque is an important animal model, the inventors switched to a SIV (Simian Immunodeficiency Virus) based LV system, previously developed by the inventors (Negre et al. (2000) Gene Ther. 7:1613-1623), which was not subjected to these post-entry restrictions and allowed efficient transduction of macaque T-cell and CD34⁺ cells. For all pseudotypes, they obtained similar infectious titers for SIV-derived pseudotypes as compared to HIV vectors.

The stability of the pseudotyped vectors in cynomolgus macaque sera was evaluated. The same quantities of pseudotyped infectious particles were mixed with fresh macaque sera and with macaque sera incubated for 1 h at 56° C. which enabled inactivating the complement system. In contrast to VSV-G LVs that were readily inactivated in fresh sera, RD114/TR-, BaEV/TR- and BaEVRLess-LV pseudotypes remained stable upon incubation with macaque sera evaluated (FIG. 11). This was confirmed for two independent macaque donors.

In order to evaluate the macaque CD34⁺ cell transduction, the inventors pre-stimulated cynomolgus macaque CD34⁺ cells derived from bone marrow with a strong cytokine cocktail (rSCF+rTPO+rFlt3-L+rIL-3+rIL-6) during 16 h. They transduced them with VSV-G, RD114/TR, BaEV/TR, BaEVRLess pseudotyped SIV-LVs at a MOI of 10 or 20 in culture wells coated with retronectin (FIG. 12). As reported for VSV-G-LV pseudotypes, they observed that they allow low level transduction of the macaque CD34⁺ cells independently of the presence of retronectin. Importantly, RD114/TR, BaEV/TR and BaEVRLess LV pseudotypes needed retronectin to transduce macaque CD34⁺ cells. BaEV/TR pseudotyped SIV-LVs at an MOI of 20 transduced up to 60% of cynomolgus macaque CD34⁺ cells while the BaEVRLess LVs showed up to 45% of transduction (FIG. 12). The transduction of rhesus macaque CD34⁺ cells was slightly different since BaEV/TR-LVs allowed the highest transduction levels (50%) and were superior over VSV-G- and BaEVRLess-LVs in efficiency (FIG. 13).

These first results indicated that BaEV/TR- and BaEVRLess-LV pseudotypes efficiently transduced cynomolgus and rhesus macaque CD34⁺ cells which means that it is possible to evaluate these vectors for pre-clinical testing of gene therapy vectors in these primate models, which are biologically very close to humans.

BaEV/TR- and BaEVRLess-LVs Allow Efficient Transduction of rIL-7 and T Cell Receptor Stimulated Human T Cells Another essential target for gene therapy is T cells. Naive T cells are 'the' gene therapy targets of interest since these are the long-living cells that when corrected might persist over years. BaEV/TR- and BaEVRLess-LVs allowed efficient transduction of rIL-7 pre-stimulated human T cells and were superior over VSV-G-LVs for the same vector doses (MOI=10) in the presence of retronectin (% transduction, BaEV/TR-LV=25-43%, BaEVRLess=25-45%, VSV-G-LV=5-15%; FIG. 14). Surprisingly, the RD114/TR-LVs allowed much lower transduction efficiency of rIL-7 pre-stimulated T cells as compared to BaEV-LVs (RD114/TR-LV=5-15%). Moreover, the BaEV/TR- and BaEVRLess-LVs allowed an efficient high transduction level of both naive and memory IL-7 prestimulated T cells (FIG. 15). Since rIL-7 is a T cell survival cytokine regulating T cell homeostasis, no naive to memory phenotypic switch is induced as compared to a T-cell receptor (TCR) stimulation which induced a switch of naive to memory T cell phenotype. Indeed, BaEV/TR- and BaEVRLess-LVs allowed transduction of IL-7 stimulated T-cells without compromising their naive phenotype. This is highly relevant for many gene therapy applications.

Up to date the majority of the clinical trials uses TCR stimulated T cells. Of high interest, the BaEV/TR- and BaEVRLess-LVs permitted up to 90% T cell gene transfer in TCR stimulated at low vector doses (MOI=10) and thus outperformed by far VSV-G- and RD114/TR-LVs for transduction of TCR prestimulated T cells (FIG. 16).

Overall, the novel BaEV/TR- and BaEVRLess-LVs are promising gene transfer tools for T cell gene therapy.

BaEV/TR- and BaEVRLess-LVs Allow Efficient Transduction of Unstimulated and BCR Stimulated Human B Cells B lymphocytes are attractive targets for gene therapy of genetic diseases associated with B-cell dysfunction. In addition, long-lasting transgene expression in B-cells is of particular interest for immunotherapy by its potential to induce specific immune activation or tolerance. Moreover, efficient delivery of genes or shRNAs for gene expression knockdown into primary human B lymphocytes would allow studying gene functions in these cells. However, primary B-cells remain very poorly transducible with VSVG-pseudotyped LVs even when stimulated into proliferation by cross-linking of CD40 in the presence of various cytokines.

Since BaEV glycoprotein pseudotyped LVs were able to transduce T cells, the inventors evaluated them for gene transfer into primary human B cells.

VSV-G-LVs were unable to transduce unstimulated resting human B cells efficiently even at high vector doses (MOI=100, VSV-G-LV<5% transduction). Of interest, RD114/TR-LVs allowed only low transduction levels of up to 8% of primary resting B cells (FIG. 17). BaEV/TR-LVs and BaEVRLess-LVs permitted highly efficient transduction of 20-30% of resting B cells and thus outperformed the VSV-G-LVs and RD114/TR-LVs by far (FIG. 17, Retronectin). Upon B cell receptor (BCR) stimulation, BaEV/TR- and BaEVRLess-LVs transduced up to 70% of the B cells while VSV-G-LV transduction efficiency did no exceed 5%. RD114/TR-LVs allowed transduction of 25% of BCR stimulated primary B cells. Of importance, BaEV/TR- and BaEVRLess-LVs transduced as well memory as naive B cells efficiently in the presence of retronectin (FIGS. 18 and 19). Of interest, primary marginal zone lymphoma (MZL) B cells were efficiently transduced by BaEV/TR- and BaEVRLess-LVs (up to 75%) in the presence of retronectin (FIG. 20).

Thus, BaEV/TR-LVs and BaEVRLess-LVs outperformed VSV-G-LVs and RD114/TR-LVs for the transduction of human healthy and cancer B cells and might be promising tools for B cell based gene and immunotherapy BaEVgp LVs Allow High-Level Transduction of Thymocytes in Early Stages of Differentiation The thymus is the primary site of T cell development and plays a key role in the induction of self-tolerance. Therefore, targeting the thymus with an antigen of interest can result in the induction of tolerance. Indeed, this has been achieved by the direct injection of soluble antigen, of viral vector harboring an antigen of interest or even of entire cells (Khoury et al. (1993) *J Exp Med.* 178:559-66, Marodon et al. (2006) *Blood* 108:2972-8, Posselt et al. (1992) *Science* 256:1321-4). Secondly, in situ correction of a genetic immunodeficiency, ZAP-70, by intra-thymus injection of a lentiviral vector expressing the correcting gene was demonstrated (Adjali et al. (2005) *J Clin Invest.* 115:2287-95).

Thymocyte differentiation is a highly regulated process that occurs via the interaction with the thymic stroma cells and cytokine stimulation (FIG. 22A). Hematopoietic stem cells (CD34+ CD1a−) are migrating from the bone marrow to the thymus where they first gain CD1a expression and lack the expression of CD8 and CD4 markers (CD8−CD4− double negative (DN) stage; 2-5% of total thymocytes). These DN cells subsequently develop into immature CD4 single positive cells (ISP) and gain expression of the pre-T cell receptor (pre-TCR; FIG. 22A). The appearance of the CD8 surface marker together with CD4 and maturation of the TCR is called the double positive (DP) stage of thymocyte development (80-90% of the total thymocytes). Upon selection in the thymus DP thymocytes develop into CD8+ CD4− (SP8) and CD8−CD4+ (SP4) thymocytes (FIG. 22A).

Because of the potential value of thymocyte gene transfer for immune modulation, it is important to develop vectors for efficient thymocyte transduction. Therefore, the inventors evaluated the performance of BaEVgp-LVs compared to the other LV pseudotypes for the transduction of all these different thymocyte subpopulations. Upon isolation of thymocytes from a human thymus, they transduced them in the presence of the survival cytokine IL-7 with VSV-G-, RD114/TR-, BaEV/TR-, and BaEVRLess-LVs encoding for the GFP reporter at an MOI of 10. For all transduction experiments retronectin coated plates were used. Three days later we determined the transduction levels by FACS in the different thymocyte subpopulations using CD4/CD8/CD3 triple staining.

VSV-G-LVs do not allow efficient transduction of all these different subpopulations reaching between 10 and 20% of transduced cells (FIG. 22B). RD114/TR-LV, BaEV/TR-LVs and BaEVRLess-LVs though allow preferential transduction of the thymocytes in the early stages of development (DN and ISP) while they still transduce the more mature to a lower level (FIG. 22B). As already detected for adult human T cells, BaEVgp LVs transduced all different thymocyte subpopulations more efficiently than the RD114/TR-LVs. Moreover, transduction with the different lentiviral vector pseudotypes had no effect on the distribution of different thymocyte subpopulations (FIG. 22C). This indicates that BaEVgp-LVs are excellent tools for transduction of thymocytes and that they are especially superior over VSV-G- and RD114/TR-LVs for the transduction of the immature DN and ISP thymocyte subpopulations.

BaEVgp-LVs Allow High-Level Transduction of Cord Blood Recent Thymocyte Emigrants It might be of high interest for T cell gene therapy or immunotherapy to genetically modify truly naive T cells, which are understood to be the cells persisting for the entire life-span of an individual. Therefore, the inventors focused on cord blood (CB) T cells since they are gaining importance in the context of allogenic CB transplantations. The majority of CB T cells are naive and provide the advantage that they represent a reduced risk of graft-versus-host disease (GVHD), a common side effect seen in bone marrow allogenic transplantation including allogenic adult T cells. In contrast to adult T cells, though, CB T cell exert a reduced graft-versus-leukemia effect.

The majority of CB T cells (70-80%) are identified by CD31, CD62L and CD45RA positive staining which is a highly immature naive T cell population and are called recent thymocyte emigrants (RTEs). Genetic modification of these cells in the context of allogenic transplantation to increase their graft-versus-leukemia effect without increasing GVHD would be beneficial (Micklethwaite et al. (2010) *Blood* 115:2695-703). Therefore, the inventors tested several lentiviral vector pseudotypes for their transduction efficiency of CB RTEs.

To conserve the T cell naive phenotype they prestimulated freshly isolated total CB T cells with the T cell survivial cytokine, IL-7, and subsequently transduced them with the different vectors: VSV-G-, RD114/TR-, BaEV/TR-, and BaEVRLess-LVs encoding the GFP reporter at an MOI of 10 or 20, except for VSV-G-LVs for which a higher vector dose (MOI of 50) was applied. FIG. 23A shows that BaEV/TR-, and BaEVRLess-LVs show a transduction efficiency highly superior (40-50% transduction) at an MOI=10 as compared to VSV-G or RD114/TR-LVs (FIG. 23A). Importantly, BaEV/TR- and BaEVRLess-LVs reached easily 65% transduction when the vector dose was 2-fold increased (MOI=20; FIG. 23A). In all cases the naive recent thymocyte emigrants (CD69L+ CD45RA+ CD31+) were transduced to the same extent as the more mature naive CB T cells (CD69L+ CD45RA+ CD31−; FIG. 23A). Moreover, transduction had no effect on the distribution of these two naive CB T cell populations (FIG. 23B).

Discussion

In this example, the inventors described efficient pseudotyping of lentiviral vectors using a novel envelope glycoprotein BaEV derived from the Baboon endogenous virus. Two mutants of this glycoprotein: the BaEV/TR chimeric glycoprotein and the BaEVRLess glycoprotein allowed a better incorporation on the LV surface as compared to the BaEVwt glycoprotein. LVs pseudotyped by these envelopes could be produced at high titers ($1 \cdot 10^7$ IU/ml). Like RD114/TR-LV pseudotypes, they were stable in human and macaque sera, which allow potential clinical perspectives for in vivo delivery of transgenes.

Regarding transduction of hCD34+ cells, BaEV mutant LV pseudotypes were superior to VSV-G and RD114/TR. First, they were able to transduce hCD34+ cells upon very low prestimulation protocols. Indeed, people currently use cytokine cocktails containing rSCF, rTPO, rFlt3-L and IL-3 but it was reported that the more hCD34+ cells are stimulated, the more they differentiate and they lose their long term hematopoietic reconstitution capacity. Furthermore, IL-3 was thought to notably increase the CD34+ differentiation. Here, the inventors showed that BaEV/TR- and BaEVRLess-LVs achieved high transduction rates of hCD34+ cells when they were prestimulated with rSCF, rTPO or rSCF and rTPO co-stimulation for a short time of 16 h. These mild cytokine stimulation protocols strongly reduced the risk of differentiation of HSCs present in the hCD34+ cell population. Of high importance, these results indicated that BaEV/TR-LV pseudotypes could transduce 10-20% of unstimulated hCD34+ cells while VSV-G-LVs and RD114/TR-LVs remained inefficient. Thus, since no cytokine stimulation is needed to achieve efficient hCD34+ cell transduction with BaEV/TR- or BaEVRLess-LVs they possibly allow to conserve better the stem cell character of hCD34+ cells.

Another important observation was that at low MOIs (5 and 10) lentiviral vector pseudotyped with BaEV/TR and BaEVRLess respectively, consistently transduced human CD34+ cells better than VSV-G LV pseudotypes at MOI of 100. The use of a lentiviral vector at a very low MOI could limit insertional mutagenesis which occurs when the proviral DNA is inserted in an oncogene of the host cells. If too many vectors integrate into the host cell genome, it could lead to genotoxicity due to host cell gene deregulation. Thus, in the case of BaEV-LVs, it would be possible to decrease significantly the vector doses to safe levels without a significant loss of the transduction rate. In contrast, for VSV-G-LVs very high vector doses were needed to allow efficient hCD34+ cell transduction.

The ability of BaEV/TR- and BaEVRLess-LV pseudotypes to highly transduce short term repopulating cells and the results on reconstitution of immunodeficient mice bone marrow and spleen with gene marked cells in all the different human cell lineages are arguments that strongly suggest they actually transduce HSCs.

Moreover, the novel BaEV/TR- and BaEVRLess-LVs are promising gene transfer tools for T cell gene therapy since they allow high transduction of IL-7 prestimulated T cells without inducing a phenotypic switch. Additionally, if one considers the need for a life time correction, it is necessary to transduce the long-lived naive T cells which are shown here to be highly susceptible to BaEV/TR- and BaEVRLess-LV mediated gene transfer and might know therefore many applications in vivo.

Finally, these BaEV/TR- and BaEVRLess-LVs represent a new tool allowing high stable gene transfer of primary quiescent B cells that now makes it possible to study with ease gene function and therapeutic gene transfer in these cells. These novel vectors may allow expression of co-stimulatory molecules such as CD40L or B7 molecules in non-dividing tumor B-cells such as B-CLLs in order to elicit immune responses against gene modified and unmodified cells. They also enable introducing DNA encoding the light and heavy chains of specific antibodies (for example antibodies specifically directed against HIV or HCV) or epitopes into autologous memory B cells in order to allow immunotherapy and tolerance induction upon reinfusion of the engineered cells.

In vivo gene delivery of lentiviral vectors displaying BaEV/TR- or BaEVRLess-LVs in HSCs, B cells or T cells would make gene therapy much easier. The advantages of in vivo gene delivery are multiple. In vivo gene transfer could target all HSCs in their stem cell niche, which creates a microenvironment regulating HSC survival and maintenance. Moreover, for the majority of diseases there is a requirement of a minimal number of gene-corrected cells to be re-infused. This requisite might be a limiting factor when treating children since CD34+ isolation results in significant loss of this target population or in bone marrow failure syndromes like Fanconi anemia, in which patients already suffer from a reduced number of hCD34+ cells early on. All these concerns might be overcome by in vivo targeted gene delivery to HSCs. Identical reasoning is possible for T and especially for B cells since the latter cells go easily into apoptosis during ex vivo culture.

In summary, the inventors have developed a novel and apparently effective pseudotype for lentiviral vectors. BaEV/TR and BaEVRLess pseudotyped LV will probably become useful for many fundamental and clinical applications because they present a lot of advantages such as very high transduction of human primary HSCs, T cells and B cells.

Sequence Identifiers Reference Table:

| SEQ ID NO: | Feature |
| --- | --- |
| 1 | Nucleic acid encoding the wild-type BaEV envelope glycoprotein |
| 2 | Wild-type BaEV envelope glycoprotein |
| 3 | Cytoplasmic tail domain of the wild-type BaEV envelope glycoprotein |
| 4 | Transmembrane domain of the wild-type BaEV envelope glycoprotein |
| 5 | Extracellular domain of the wild-type BaEV envelope glycoprotein |
| 6 | Fusion inhibitory R peptide of the wild-type BaEV envelope glycoprotein |
| 7 | Modified BaEV envelope glycoprotein wherein the cytoplasmic tail domain is devoid of the fusion inhibitory R peptide (BaEVRLess) |
| 8 | Cytoplasmic tail domain of the wild-type MLV envelope glycoprotein |

| SEQ ID NO: | Feature |
|---|---|
| 9 | Fusion of the transmembrane and extracellular domain of the BaEV envelope glycoprotein and the cytoplasmic tail domain of the MLV envelope glycoprotein (BaEV/TR) |
| 10 | Human wild-type SCF |
| 11 | Human wild-type TPO |
| 12 | Human wild-type IL-2 |
| 13 | Human wild-type IL-7 |
| 14 | Human wild-type IL-15 |
| 15 | Human wild-type Flt3-L |

The invention claimed is:

1. A pseudotyped viral vector particle for transferring biological material into cells, wherein said viral vector particle is a lentiviral vector particle and comprises at least:
   - a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein; or
   - a modified BaEV envelope glycoprotein wherein the cytoplasmic tail domain is devoid of the fusion inhibitory R peptide.

2. The pseudotyped viral vector particle according to claim 1, wherein the lentiviral vector particle is selected from the group consisting of HIV and SIV.

3. The pseudotyped viral vector particle according to claim 1, wherein the biological material is one or more nucleic acids.

4. The pseudotyped viral vector particle according to claim 1, wherein said viral vector particle further displays at least one cytokine selected from the group consisting of stem cell factor (SCF), thrombopoietin (TPO), IL-2, IL-15 and IL-7.

5. The pseudotyped viral vector particle according to claim 1, wherein the pseudotyped viral vector particle is intended for transferring biological material into hematopoietic cells.

6. A method for treating a hematopoietic disorder or an autoimmune disease in a subject in need thereof comprising administering a therapeutically effective amount of a pseudotyped viral vector particle according to claim 1.

7. The method according to claim 6, wherein the hematopoietic disorder is selected from the group consisting of Fanconi anemia, hemophilia, beta-thalassemia, Wiskott-Aldrich syndrome, X-linked severe combined immunodeficiency, adenosine-deaminase deficiency, chronic granulomatous disease and adrenoleukodystrophy.

8. A method for producing a pseudotyped viral vector particle comprising:
   a) transfecting a cell with:
      (i) at least one first nucleic acid sequence comprising a packaging competent lentiviral derived genome;
      (ii) at least one second nucleic acid sequence comprising a cDNA encoding core proteins from said lentivirus, and
      (iii) at least one third nucleic acid sequence comprising a cDNA encoding:
         a chimeric envelope glycoprotein which comprises or consists in a fusion of the transmembrane and extracellular domain of a baboon endogenous retrovirus (BaEV) envelope glycoprotein and the cytoplasmic tail domain of a murine leukemia virus (MLV) envelope glycoprotein, as defined above; or
         a modified BaEV envelope glycoprotein wherein the cytoplasmic tail domain is devoid of the fusion inhibitory R peptide, as defined above;
   to yield a producer cell;

b) maintaining the producer cell in culture for sufficient time to allow expression of the cDNAs to produce the encoded proteins; and c) allowing the encoded proteins to form pseudotyped viral vector particles.

9. A medicament comprising a pseudotyped viral vector particle as defined in claim 1 as active ingredient.

10. A method for transducing a hematopoietic cell comprising contacting the hematopoietic cell with a pseudotyped viral vector particle as defined in claim 1 under conditions to effect the transduction of the hematopoietic cell by the pseudotyped viral vector particle.

11. The method according to claim 10, wherein the hematopoietic cell is selected from the group consisting of hematopoietic stem cells, progenitor CD34+ cells, very early progenitor CD34+ cells, B-cell CD19+ progenitors, myeloid progenitor CD13+ cells, T lymphocytes, B lymphocytes, monocytes, dendritic cells, peripheral blood CD34+ cells, cancer B cells (BCLL), marginal zone lymphoma (MZL) B cells and thymocytes.

12. The method according to claim 11 wherein the hematopoietic cell is not prestimulated with at least one cytokine.

13. A stable virus packaging cell line producing the pseudotyped viral vector particle as defined in claim 1.

* * * * *

SEQUENCE LISTING

<160> NUMBER OF SEQ ID NOS: 15

<210> SEQ ID NO 1
<211> LENGTH: 1692
<212> TYPE: DNA
<213> ORGANISM: Baboon endogenous virus

<400> SEQUENCE: 1

```
atgggattca caacaaagat aatcttctta tacaacctag tactggtcta cgcggggttt      60
gacgaccctc gcaaagccat agaactagta caaaagcgat atggccgacc atgcgattgc     120
agcggaggac aagtgtccga gcccccgtca gacagggtca gtcaagtgac ttgctcaggc     180
aagacagctt acttaatgcc cgaccaaaga tggaaatgta agtcaattcc aaaagacacc     240
tccccaagcg ggccactcca agagtgcccc tgtaattctt accagtcctc agtacacagt     300
tcttgttata cctcatacca acaatgcaga tcaggcaata agacatatta tcggctact      360
ctgctaaaaa cacaaactgg gggcaccagt gatgtacaag tattaggatc caccaacaaa     420
cttatacaat ctccctgtaa tggcataaaa gggcagtcta tttgctggag cactacagct     480
cctatccacg tctctgatgg aggaggtcca ttagacacca aagaattaa aagtgttcag      540
agaaaactgg aagaaattca taagccccta tatcctgaac ttcagtatca cccttggcc      600
atacctaagg ttagagataa cctcatggtc gatgcccaga cttaaacat tctcaatgcc      660
acttacaact actcctaat gtccaacacg agcctagtgg acgactgttg gctttgtta       720
aaattaggtc ccctactcc cctcgcaata cctaacttcc tattatccta cgtgactcgc      780
tcctcggata atatctcttg tttaataatt cccccccttc tagttcaacc gatgcagttt     840
tccaattcat cttgcctctt ttcccccctcc tacaacagta cagaagaaat agatctaggc     900
catgttgcct tcagcaactg tacctccata accaatgtca ccgtcccat atgcgctgta      960
aatggttcgg tctttctctg tggcaataac atggcataca cttatctacc cacgaactgg    1020
acggggcttt gcgtcctagc aactctcctc cccgacattg acatcattcc cggagatgaa    1080
ccggtcccca tccctgctat tgatcattt atatatagac taacgggc catacagttt       1140
attcctttac tagcagggct agggatcacc gcagccttca aacaggagc tacaggccta     1200
ggtgtctctg tgacccaata tacaaaatta tctaatcagc taatttctga tgtacaaatc    1260
ttatctagca ccatacaaga tctgcaagat caagtagact cattagccga agtggttctc    1320
cagaacagaa gggggctaga tctacttaca gcagaacaag gaggaatctg tttagccctg    1380
caagaaaaat gctgctttta tgttaacaag tcagggattg tgagagacaa aataaaaacc    1440
ttacaagaag aactagaaag acgtagaaaa gatctagctt ccaacccact ttggactggg    1500
cttcaagggc tcctccctta cctcctgccc tttcttggcc ctctacttac cctcctgctc    1560
ttactcacca ttgggccgtg catttttaac cgtctaaccg cttttattaa tgataagtta    1620
aacataatac acgctatggt gctaaccaa cagtatcagg tgctcagaac cgatgaagaa     1680
```

```
gctcaagatt ga                                                      1692
```

<210> SEQ ID NO 2
<211> LENGTH: 563
<212> TYPE: PRT
<213> ORGANISM: Baboon endogenous virus
<220> FEATURE:
<221> NAME/KEY: MISC_FEATURE
<222> LOCATION: (1)..(506)
<223> OTHER INFORMATION: extracellular domain
<220> FEATURE:
<221> NAME/KEY: MISC_FEATURE
<222> LOCATION: (507)..(529)
<223> OTHER INFORMATION: transmembrane domain
<220> FEATURE:
<221> NAME/KEY: MISC_FEATURE
<222> LOCATION: (530)..(563)
<223> OTHER INFORMATION: cytoplasmic tail
<220> FEATURE:
<221> NAME/KEY: MISC_FEATURE
<222> LOCATION: (547)..(563)
<223> OTHER INFORMATION: R peptide

<400> SEQUENCE: 2

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gly Gln Val Ser Glu Pro
        35                  40                  45

Pro Ser Asp Arg Val Ser Gln Val Thr Cys Ser Gly Lys Thr Ala Tyr
    50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
    130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

```
Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Cys Gly Asn Asn Met Ala Tyr Thr Tyr Leu
                325                 330                 335

Pro Thr Asn Trp Thr Gly Leu Cys Val Leu Ala Thr Leu Leu Pro Asp
                340                 345                 350

Ile Asp Ile Ile Pro Gly Asp Glu Pro Val Pro Ile Pro Ala Ile Asp
                355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
                420                 425                 430

Asp Ser Leu Ala Glu Val Val Leu Gln Asn Arg Arg Gly Leu Asp Leu
                435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Lys Asp Leu Ala Ser Asn Pro
                485                 490                 495

Leu Trp Thr Gly Leu Gln Gly Leu Leu Pro Tyr Leu Leu Pro Phe Leu
                500                 505                 510

Gly Pro Leu Leu Thr Leu Leu Leu Leu Thr Ile Gly Pro Cys Ile
                515                 520                 525

Phe Asn Arg Leu Thr Ala Phe Ile Asn Asp Lys Leu Asn Ile Ile His
    530                 535                 540

Ala Met Val Leu Thr Gln Gln Tyr Gln Val Leu Arg Thr Asp Glu Glu
545                 550                 555                 560

Ala Gln Asp

<210> SEQ ID NO 3
<211> LENGTH: 34
<212> TYPE: PRT
<213> ORGANISM: Baboon endogenous virus

<400> SEQUENCE: 3

Asn Arg Leu Thr Ala Phe Ile Asn Asp Lys Leu Asn Ile Ile His Ala
1               5                   10                  15

Met Val Leu Thr Gln Gln Tyr Gln Val Leu Arg Thr Asp Glu Glu Ala
            20                  25                  30

Gln Asp

<210> SEQ ID NO 4
<211> LENGTH: 23
<212> TYPE: PRT
<213> ORGANISM: Baboon endogenous virus

<400> SEQUENCE: 4

Tyr Leu Leu Pro Phe Leu Gly Pro Leu Leu Thr Leu Leu Leu Leu
```

-continued

```
               1               5                   10                  15
Thr Ile Gly Pro Cys Ile Phe
                20
```

<210> SEQ ID NO 5
<211> LENGTH: 506
<212> TYPE: PRT
<213> ORGANISM: Baboon endogenous virus

<400> SEQUENCE: 5

```
Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
                20                  25                  30

Arg Tyr Gly Arg Pro Cys Asp Cys Ser Gly Gly Gln Val Ser Glu Pro
            35                  40                  45

Pro Ser Asp Arg Val Ser Gln Val Thr Cys Ser Gly Lys Thr Ala Tyr
        50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
        115                 120                 125

Thr Ser Asp Val Gln Val Leu Gly Ser Thr Asn Lys Leu Ile Gln Ser
130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350
```

```
Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
                420                 425                 430

Asp Ser Leu Ala Glu Val Val Leu Gln Asn Arg Arg Gly Leu Asp Leu
            435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Lys Asp Leu Ala Ser Asn Pro
                485                 490                 495

Leu Trp Thr Gly Leu Gln Gly Leu Leu Pro
                500                 505

<210> SEQ ID NO 6
<211> LENGTH: 17
<212> TYPE: PRT
<213> ORGANISM: Baboon endogenous virus

<400> SEQUENCE: 6

Val Leu Thr Gln Gln Tyr Gln Val Leu Arg Thr Asp Glu Glu Ala Gln
1               5                   10                  15

Asp

<210> SEQ ID NO 7
<211> LENGTH: 546
<212> TYPE: PRT
<213> ORGANISM: Artificial
<220> FEATURE:
<223> OTHER INFORMATION: Synthetic protein BaEVRLess

<400> SEQUENCE: 7

Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
                20                  25                  30

Arg Tyr Gly Arg Pro Cys Asp Cys Ser Gly Gly Gln Val Ser Glu Pro
            35                  40                  45

Pro Ser Asp Arg Val Ser Gln Val Thr Cys Ser Gly Lys Thr Ala Tyr
        50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
                100                 105                 110

Asn Lys Thr Tyr Tyr Thr Ala Thr Leu Leu Lys Thr Gln Thr Gly Gly
            115                 120                 125

Thr Ser Asp Val Gln Val Leu Gly Ser Thr Asn Lys Leu Ile Gln Ser
        130                 135                 140
```

```
Pro Cys Asn Gly Ile Lys Gly Gln Ser Ile Cys Trp Ser Thr Thr Ala
145                 150                 155                 160

Pro Ile His Val Ser Asp Gly Gly Pro Leu Asp Thr Thr Arg Ile
            165                 170                 175

Lys Ser Val Gln Arg Lys Leu Glu Ile His Lys Ala Leu Tyr Pro
        180                 185                 190

Glu Leu Gln Tyr His Pro Leu Ala Ile Pro Lys Val Arg Asp Asn Leu
            195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285

Pro Ser Tyr Asn Ser Thr Glu Glu Ile Asp Leu Gly His Val Ala Phe
290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Thr Ile Gly Pro Cys Ile
        515                 520                 525

Phe Asn Arg Leu Thr Ala Phe Ile Asn Asp Lys Leu Asn Ile Ile His
    530                 535                 540

Ala Met
545
```

<210> SEQ ID NO 8
<211> LENGTH: 33
<212> TYPE: PRT
<213> ORGANISM: Murine leukemia virus

<400> SEQUENCE: 8

```
Asn Arg Leu Val Gln Phe Val Lys Asp Arg Ile Ser Val Val Gln Ala
1               5                   10                  15

Leu Val Leu Thr Gln Gln Tyr His Gln Leu Lys Pro Leu Glu Tyr Glu
            20                  25                  30

Pro
```

<210> SEQ ID NO 9
<211> LENGTH: 562
<212> TYPE: PRT
<213> ORGANISM: Artificial
<220> FEATURE:
<223> OTHER INFORMATION: Synthetic protein BaEV/TR

<400> SEQUENCE: 9

```
Met Gly Phe Thr Thr Lys Ile Ile Phe Leu Tyr Asn Leu Val Leu Val
1               5                   10                  15

Tyr Ala Gly Phe Asp Asp Pro Arg Lys Ala Ile Glu Leu Val Gln Lys
            20                  25                  30

Arg Tyr Gly Arg Pro Cys Asp Cys Ser Gly Gln Val Ser Glu Pro
            35                  40                  45

Pro Ser Asp Arg Val Ser Gln Val Thr Cys Ser Gly Lys Thr Ala Tyr
        50                  55                  60

Leu Met Pro Asp Gln Arg Trp Lys Cys Lys Ser Ile Pro Lys Asp Thr
65                  70                  75                  80

Ser Pro Ser Gly Pro Leu Gln Glu Cys Pro Cys Asn Ser Tyr Gln Ser
                85                  90                  95

Ser Val His Ser Ser Cys Tyr Thr Ser Tyr Gln Gln Cys Arg Ser Gly
            100                 105                 110

Asn Lys Thr Tyr Tyr Thr Ala Thr Leu Leu Lys Thr Gln Thr Gly Gly
            115                 120                 125

Thr Ser Asp Val Gln Val Leu Gly Ser Thr Asn Lys Leu Ile Gln Ser
        130                 135                 140

Pro Cys Asn Gly Ile Lys Gly Gln Ser Ile Cys Trp Ser Thr Thr Ala
145                 150                 155                 160

Pro Ile His Val Ser Asp Gly Gly Gly Pro Leu Asp Thr Thr Arg Ile
                165                 170                 175

Lys Ser Val Gln Arg Lys Leu Glu Glu Ile His Lys Ala Leu Tyr Pro
            180                 185                 190

Glu Leu Gln Tyr His Pro Leu Ala Ile Pro Lys Val Arg Asp Asn Leu
        195                 200                 205

Met Val Asp Ala Gln Thr Leu Asn Ile Leu Asn Ala Thr Tyr Asn Leu
    210                 215                 220

Leu Leu Met Ser Asn Thr Ser Leu Val Asp Asp Cys Trp Leu Cys Leu
225                 230                 235                 240

Lys Leu Gly Pro Pro Thr Pro Leu Ala Ile Pro Asn Phe Leu Leu Ser
                245                 250                 255

Tyr Val Thr Arg Ser Ser Asp Asn Ile Ser Cys Leu Ile Ile Pro Pro
            260                 265                 270

Leu Leu Val Gln Pro Met Gln Phe Ser Asn Ser Ser Cys Leu Phe Ser
        275                 280                 285
```

-continued

```
Pro Ser Tyr Asn Ser Thr Glu Glu Ile Asp Leu Gly His Val Ala Phe
    290                 295                 300

Ser Asn Cys Thr Ser Ile Thr Asn Val Thr Gly Pro Ile Cys Ala Val
305                 310                 315                 320

Asn Gly Ser Val Phe Leu Cys Gly Asn Asn Met Ala Tyr Thr Tyr Leu
                325                 330                 335

Pro Thr Asn Trp Thr Gly Leu Cys Val Leu Ala Thr Leu Leu Pro Asp
            340                 345                 350

Ile Asp Ile Ile Pro Gly Asp Glu Pro Val Pro Ile Pro Ala Ile Asp
        355                 360                 365

His Phe Ile Tyr Arg Pro Lys Arg Ala Ile Gln Phe Ile Pro Leu Leu
    370                 375                 380

Ala Gly Leu Gly Ile Thr Ala Ala Phe Thr Thr Gly Ala Thr Gly Leu
385                 390                 395                 400

Gly Val Ser Val Thr Gln Tyr Thr Lys Leu Ser Asn Gln Leu Ile Ser
                405                 410                 415

Asp Val Gln Ile Leu Ser Ser Thr Ile Gln Asp Leu Gln Asp Gln Val
            420                 425                 430

Asp Ser Leu Ala Glu Val Val Leu Gln Asn Arg Arg Gly Leu Asp Leu
        435                 440                 445

Leu Thr Ala Glu Gln Gly Gly Ile Cys Leu Ala Leu Gln Glu Lys Cys
    450                 455                 460

Cys Phe Tyr Val Asn Lys Ser Gly Ile Val Arg Asp Lys Ile Lys Thr
465                 470                 475                 480

Leu Gln Glu Glu Leu Glu Arg Arg Lys Asp Leu Ala Ser Asn Pro
                485                 490                 495

Leu Trp Thr Gly Leu Gln Gly Leu Leu Pro Tyr Leu Leu Pro Phe Leu
            500                 505                 510

Gly Pro Leu Leu Thr Leu Leu Leu Leu Thr Ile Gly Pro Cys Ile
        515                 520                 525

Phe Asn Arg Leu Val Gln Phe Val Lys Asp Arg Ile Ser Val Val Gln
    530                 535                 540

Ala Leu Val Leu Thr Gln Gln Tyr His Gln Leu Lys Pro Leu Glu Tyr
545                 550                 555                 560

Glu Pro
```

<210> SEQ ID NO 10
<211> LENGTH: 273
<212> TYPE: PRT
<213> ORGANISM: Homo sapiens

<400> SEQUENCE: 10

```
Met Lys Lys Thr Gln Thr Trp Ile Leu Thr Cys Ile Tyr Leu Gln Leu
1               5                   10                  15

Leu Leu Phe Asn Pro Leu Val Lys Thr Glu Gly Ile Cys Arg Asn Arg
            20                  25                  30

Val Thr Asn Asn Val Lys Asp Val Thr Lys Leu Val Ala Asn Leu Pro
        35                  40                  45

Lys Asp Tyr Met Ile Thr Leu Lys Tyr Val Pro Gly Met Asp Val Leu
    50                  55                  60

Pro Ser His Cys Trp Ile Ser Glu Met Val Val Gln Leu Ser Asp Ser
65                  70                  75                  80

Leu Thr Asp Leu Leu Asp Lys Phe Ser Asn Ile Ser Glu Gly Leu Ser
                85                  90                  95
```

```
Asn Tyr Ser Ile Ile Asp Lys Leu Val Asn Ile Val Asp Asp Leu Val
            100                 105                 110

Glu Cys Val Lys Glu Asn Ser Ser Lys Asp Leu Lys Lys Ser Phe Lys
            115                 120                 125

Ser Pro Glu Pro Arg Leu Phe Thr Pro Glu Glu Phe Phe Arg Ile Phe
130                 135                 140

Asn Arg Ser Ile Asp Ala Phe Lys Asp Phe Val Val Ala Ser Glu Thr
145                 150                 155                 160

Ser Asp Cys Val Val Ser Ser Thr Leu Ser Pro Glu Lys Asp Ser Arg
                165                 170                 175

Val Ser Val Thr Lys Pro Phe Met Leu Pro Pro Val Ala Ala Ser Ser
            180                 185                 190

Leu Arg Asn Asp Ser Ser Ser Asn Arg Lys Ala Lys Asn Pro Pro
            195                 200                 205

Gly Asp Ser Ser Leu His Trp Ala Ala Met Ala Leu Pro Ala Leu Phe
        210                 215                 220

Ser Leu Ile Ile Gly Phe Ala Phe Gly Ala Leu Tyr Trp Lys Lys Arg
225                 230                 235                 240

Gln Pro Ser Leu Thr Arg Ala Val Glu Asn Ile Gln Ile Asn Glu Glu
                245                 250                 255

Asp Asn Glu Ile Ser Met Leu Gln Glu Lys Glu Arg Glu Phe Gln Glu
            260                 265                 270

Val

<210> SEQ ID NO 11
<211> LENGTH: 353
<212> TYPE: PRT
<213> ORGANISM: Homo sapiens

<400> SEQUENCE: 11

Met Glu Leu Thr Glu Leu Leu Val Val Met Leu Leu Leu Thr Ala
1               5                   10                  15

Arg Leu Thr Leu Ser Ser Pro Ala Pro Pro Ala Cys Asp Leu Arg Val
            20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
65                  70                  75                  80

Ala Gln Asp Ile Leu Gly Ala Val Thr Leu Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
    130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
            180                 185                 190
```

Asn Glu Leu Pro Asn Arg Thr Ser Gly Leu Leu Glu Thr Asn Phe Thr
            195                 200                 205

Ala Ser Ala Arg Thr Thr Gly Ser Gly Leu Leu Lys Trp Gln Gln Gly
    210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
            260                 265                 270

Asp Ile Ser Ser Gly Thr Ser Asp Thr Gly Ser Leu Pro Pro Asn Leu
            275                 280                 285

Gln Pro Gly Tyr Ser Pro Ser Pro Thr His Pro Pro Thr Gly Gln Tyr
        290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
            340                 345                 350

Gly

<210> SEQ ID NO 12
<211> LENGTH: 153
<212> TYPE: PRT
<213> ORGANISM: Homo sapiens

<400> SEQUENCE: 12

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 13
<211> LENGTH: 177
<212> TYPE: PRT
<213> ORGANISM: Homo sapiens

<400> SEQUENCE: 13

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
            85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 14
<211> LENGTH: 136
<212> TYPE: PRT
<213> ORGANISM: Homo sapiens

<400> SEQUENCE: 14

Met Asp Phe Gln Val Gln Ile Phe Ser Phe Leu Leu Ile Ser Ala Ser
1               5                   10                  15

Val Ile Met Ser Arg Ala Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
            85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser
    130                 135

<210> SEQ ID NO 15
<211> LENGTH: 235
<212> TYPE: PRT
<213> ORGANISM: Homo sapiens

<400> SEQUENCE: 15

Met Thr Val Leu Ala Pro Ala Trp Ser Pro Thr Thr Tyr Leu Leu Leu

```
1               5                  10                 15
Leu Leu Leu Leu Ser Ser Gly Leu Ser Gly Thr Gln Asp Cys Ser Phe
            20                  25                 30

Gln His Ser Pro Ile Ser Ser Asp Phe Ala Val Lys Ile Arg Glu Leu
            35                  40                 45

Ser Asp Tyr Leu Leu Gln Asp Tyr Pro Val Thr Val Ala Ser Asn Leu
    50                  55                 60

Gln Asp Glu Glu Leu Cys Gly Gly Leu Trp Arg Leu Val Leu Ala Gln
65                  70                  75                 80

Arg Trp Met Glu Arg Leu Lys Thr Val Ala Gly Ser Lys Met Gln Gly
            85                  90                 95

Leu Leu Glu Arg Val Asn Thr Glu Ile His Phe Val Thr Lys Cys Ala
            100                 105                110

Phe Gln Pro Pro Pro Ser Cys Leu Arg Phe Val Gln Thr Asn Ile Ser
            115                 120                125

Arg Leu Leu Gln Glu Thr Ser Glu Gln Leu Val Ala Leu Lys Pro Trp
130             135                 140

Ile Thr Arg Gln Asn Phe Ser Arg Cys Leu Glu Leu Gln Cys Gln Pro
145             150                 155                160

Asp Ser Ser Thr Leu Pro Pro Pro Trp Ser Pro Arg Pro Leu Glu Ala
            165                 170                175

Thr Ala Pro Thr Ala Pro Gln Pro Pro Leu Leu Leu Leu Leu Leu Leu
            180                 185                190

Pro Val Gly Leu Leu Leu Leu Ala Ala Ala Trp Cys Leu His Trp Gln
            195                 200                205

Arg Thr Arg Arg Arg Thr Pro Arg Pro Gly Glu Gln Val Pro Pro Val
    210                 215                220

Pro Ser Pro Gln Asp Leu Leu Leu Val Glu His
225             230                 235
```